United States Patent
Graham et al.

(10) Patent No.: US 9,265,738 B2
(45) Date of Patent: Feb. 23, 2016

(54) SMALL MOLECULE CMKLR1 ANTAGONISTS IN DEMYELINATING DISEASE

(71) Applicant: The Board of Trustees of the Leland Stanford Junior University, Palo Alto, CA (US)

(72) Inventors: Kareem Graham, Atlanta, GA (US); Jian Zhang, Fremont, CA (US); Eugene C. Butcher, Portola Valley, CA (US); Brian A. Zabel, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 11 days.

(21) Appl. No.: 14/372,194

(22) PCT Filed: Jan. 15, 2013

(86) PCT No.: PCT/US2013/021588
§ 371 (c)(1),
(2) Date: Jul. 14, 2014

(87) PCT Pub. No.: WO2013/109543
PCT Pub. Date: Jul. 25, 2013

(65) Prior Publication Data
US 2015/0025153 A1   Jan. 22, 2015

Related U.S. Application Data

(60) Provisional application No. 61/589,146, filed on Jan. 20, 2012.

(51) Int. Cl.
*A61K 31/14* (2006.01)
*A61K 31/135* (2006.01)
(Continued)

(52) U.S. Cl.
CPC ............... *A61K 31/14* (2013.01); *A61K 31/12* (2013.01)

(58) Field of Classification Search
CPC ..... A61K 31/14; A61K 31/135; A61K 31/166
USPC .................................................. 514/643, 682
See application file for complete search history.

(56) References Cited

U.S. PATENT DOCUMENTS

2004/0122051 A1   6/2004 Pratt
2007/0286863 A1   12/2007 Sinal et al.
(Continued)

OTHER PUBLICATIONS

Baggiolini; et al., "Blocking chemokine receptors", J. Exp. Med (Oct. 1997), 186(8):1189-91.
(Continued)

*Primary Examiner* — Kamal Saeed
*Assistant Examiner* — Janet L Coppins
(74) *Attorney, Agent, or Firm* — Bozicevic, Field & Francis LLP; Pamela J. Sherwood

(57) ABSTRACT

Compounds and methods are provided for decreasing demyelinating inflammatory disease in a subject by inhibiting the activity of chemokine-like receptor 1 (CMKLR1). In some embodiments such methods include treating demyelinating inflammatory disease in a subject by administering an agent that antagonizes the activity of chemokine-like receptor 1 (CMKLR1) and/or a CMKLR1 ligand (e.g., chemerin or other endogenous CMKLR1 ligands). Candidate compounds include, without limitation, analogs and variants of 2-(alpha-naphthoyl)ethyltrimethylammonium iodide.

9 Claims, 16 Drawing Sheets

(51) Int. Cl.
*A61K 31/166* (2006.01)
*A61K 31/12* (2006.01)

(56) References Cited

U.S. PATENT DOCUMENTS

2009/0076019 A1* 3/2009 Tyers ............... A61K 31/164 514/252.13
2009/0280113 A1 11/2009 Graham et al.

OTHER PUBLICATIONS

Hasturk; et al., "RvE1 protects from local inflammation and osteoclast-mediated bone destruction in periodontitis", FASEB J. (Feb. 2006), 20(2):401-3.

"*Homo sapiens* ChemR23 gene", GenBank, downloaded Nov. 25, 2014, Y14838.1, 2 pgs.

"*Homo sapiens* retinoic acid receptor responder (tazarotene induced) 2 (RARRES2), mRNA", GenBank, downloaded Nov. 25, 2014, NM_002889.3, 4 pgs.

Samson; et al., "HChemR23, a putative chemoattractant receptor, is expressed in monocyte-derived dendritic cells and macrophages and is a coreceptor for SIV and some primary HIV-1 strains", Eur. J. Immunol. (1998), 28 (5):1689-700.

Serhan, "Lipoxins and aspirin-triggered 15-epi-lipoxins are the first lipid mediators of endogenous anti-inflammation and resolution", Prostaglandins Leukot Essent Fatty Acids (Sep.-Oct. 2005), 73(3-4):141-62.

\* cited by examiner

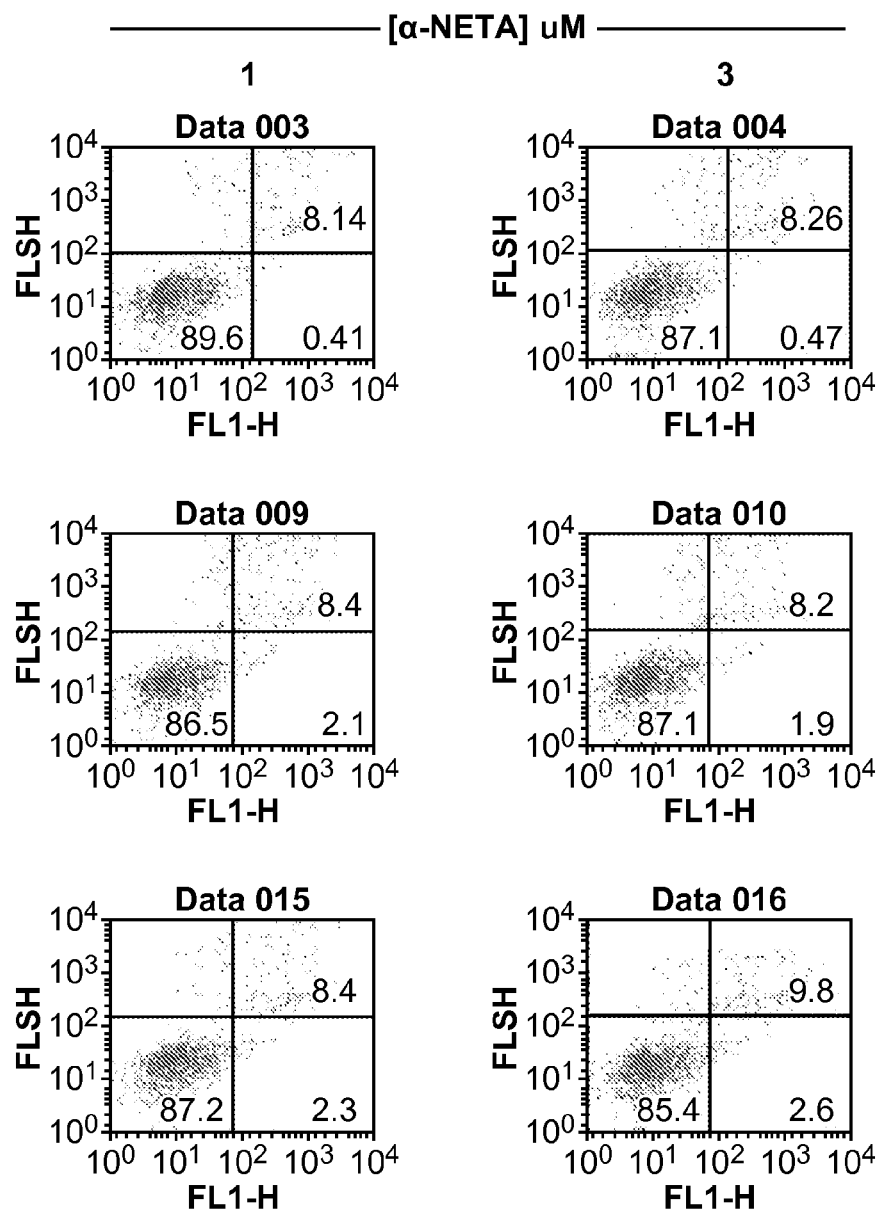
FIG. 11 (Cont. 1)

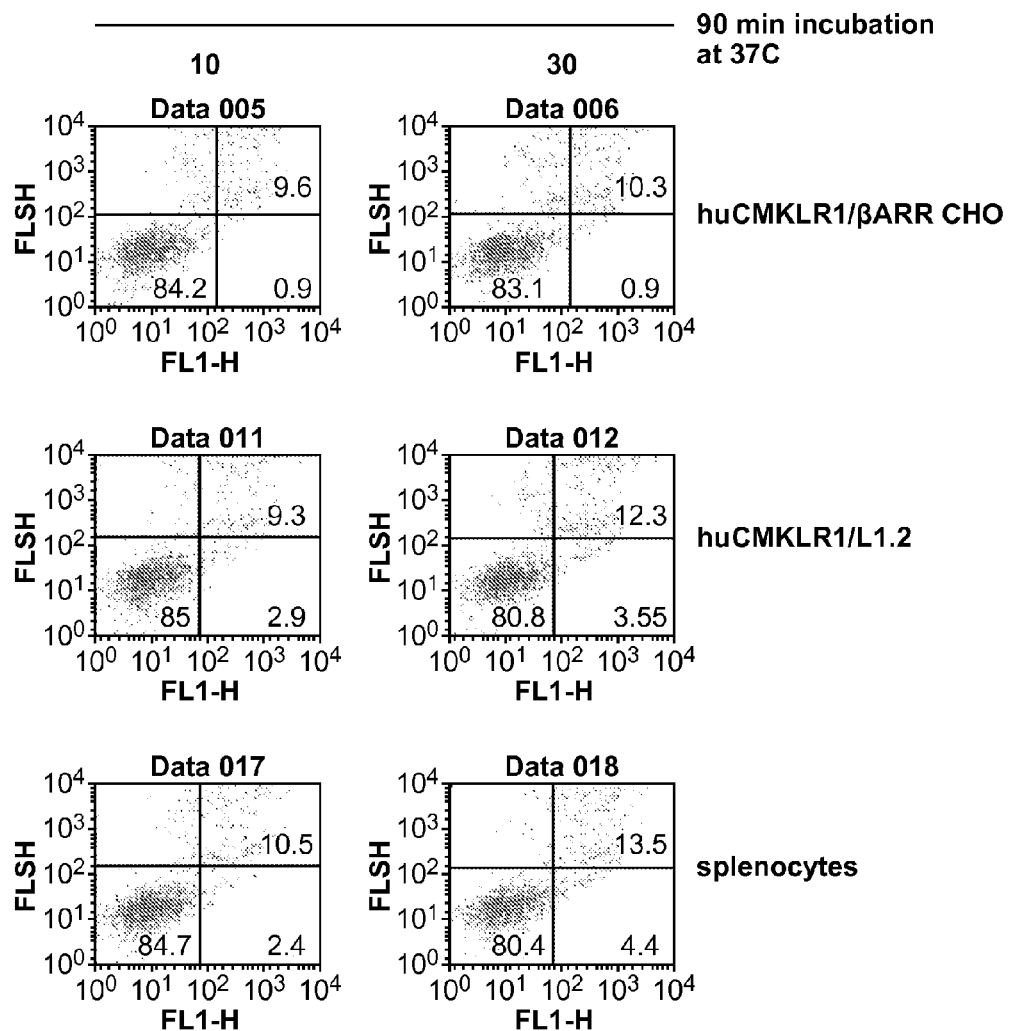
FIG. 11 (Cont. 2)

SMALL MOLECULE CMKLR1 ANTAGONISTS IN DEMYELINATING DISEASE

STATEMENT REGARDING FEDERALLY SPONSORED RESEARCH

This invention was made with government support under Grant No. AI079320 awarded by National Institutes of Health, and Grant No. W81XWH-11-1-0512 awarded by The Department of Defense Congressionally Directed Medical Research Program. The government has certain rights in the invention.

INTRODUCTION

Human chemokine-like receptor-1 (CMKLR1), a recently de-orphaned G-protein-coupled receptor (GPCR), is specifically expressed on in vitro monocyte-derived dendritic cells, ex vivo macrophages, and circulating plasmacytoid dendritic cells (pDCs), for example see Zabel et al. J Immunol (2005) 174(1):244-51; Vermi et al. J Exp Med (2005) 201(4):509-15. The natural ligand for CMKLR1, chemerin, was recently discovered; Wittamer et al., J Exp Med (2003) 198(7): 977-85; Meder et al., FEBS Lett (2003) 555(3):495-9. Chemerin has been isolated from ascitic fluid (ovarian carcinoma), inflamed synovial fluid, hemofiltrate, and normal serum. Chemerin, a heparin binding protein, initially exists in its pro-form, which is 163 amino acids long. Cleavage of pro-chemerin by serine proteases of inflammatory, coagulation, and fibrinolytic cascades results in the loss of the last 6-11 C-terminal amino acids. This proteolytic cleavage, which can be at a number of different sites in pro-chemerin, generates active chemerin and leads to a potent increase in ligand activity. This results in the increased migration of CMKLR1 bearing cells (e.g., macrophages) to chemerin; Wittamer et al., J Immunol (2005) 175(1):487-93, Zabel et al., J Biol Chem (2005) 280(41): 34661-6. Chemerin thus acts as a macrophage and dendritic cell (DC) recruiting factor through its interaction with CMKLR1.

While CMKLR1 does not bind to chemokines, it has been reported that resolvin E1 (RvE1), a bioactive lipid generated upon aspirin-triggered enzymatic processing of omega-3 fatty acids, is a lipid ligand for CMKLR1; Hasturk, et al. FASEB J. (2006) 20(2):401-3; Serhan Prostaglandins Leukot Essent Fatty Acids. (2005) 73(3-4):141-62.

Relevant Literature

The use of small molecules to block chemoattractant receptors is reviewed by Baggiolini and Moser (1997) J. Exp. Med. 186:1189-1191.

The sequence of chemerin (retinoic acid receptor responder 2 (RARRES2) II; tazarotene induced gene 2 product (TIG2)) may be found in Genbank, accession number NM_002889. The sequence of CMKLR1 may be found in Genbank, accession number Y14838, and is described by Samson et al. (1998) Eur J Immunol. 28(5):1689-700. The sequence of a CMKLR1 ligand, mammalian chemerin, may be found in Genbank, accession number NM_002889. Methods of modulating adipogenesis by interfering with the activity of CMKLR1 are described in U.S. Patent Publication 2007-0286863, herein specifically incorporated by reference.

SUMMARY

The present invention is drawn to compositions and methods for interfering with the biological processes associated with CMKLR1 signaling, which processes include, without limitation, regulation of adipogenesis and demyelinating inflammatory disease. In some embodiments, inhibitors of CMKLR1 are provided, which inhibitors are useful for the treatment or prevention of MS and other diseases, e.g. experimental animal models such as experimental autoimmune encephalomyelitis (EAE). Blocking CMKLR1 signaling may also decrease fat accumulation and adipocyte metabolism.

Inhibitors of CMKLR1 include, but are not limited to, agents that interfere with the interaction of CMKLR1 with its natural ligands, agents that reduce CMKLR1 expression (e.g., by reducing transcription or by inducing cell surface receptor desensitization and/or internalization), agents that reduce expression of endogenous ligands of CMKLR1, and agents that inhibit intracellular signals initiated by the binding of CMKLR1 with its ligands. Inhibitors include small molecules. In certain embodiments, the inhibitor is 2-(alpha-naphthoyl)ethyltrimethylammonium iodide or an analog or derivative thereof.

In some embodiments a pharmaceutical formulation of a CMKLR1 inhibitor is provided, where the formulation comprises an effective dose of the inhibitor and a pharmaceutically acceptable excipient. The formulation maybe prepared for the desired route of administration, e.g. oral, parenteral, topical, etc., usually parenteral. The inhibitor may be 2-(alpha-naphthoyl)ethyltrimethylammonium iodide or an analog or derivative thereof.

The present invention is also drawn to methods of screening for agents that can decrease demyelinating inflammatory disease when administered to a subject. In general, the screening method is designed to determine whether an agent can antagonize CMKLR1 activity in a cell. In certain embodiments, a cell expressing CMKLR1 (e.g., cells that normally express CMKLR1 or those that are genetically engineered to express CMKLR1) is contacted to a candidate agent and its response to a CMKLR1 ligand(s) is evaluated (e.g., chemotaxis, receptor/ligand binding, target gene expression, signaling responses, etc.). In certain other embodiments, a cell expressing CMKLR1 or a ligand is contacted to an agent and the expression level of CMKLR1 or its ligand is evaluated. Candidate compounds include, without limitation, analogs and variants of 2-(alpha-naphthoyl)ethyltrimethylammonium iodide.

BRIEF DESCRIPTION OF THE DRAWINGS

FIG. 10 shows a graph illustrating specificity in which aNETA does not inhibit C5aR-dependent mouse BM neutrophil chemotaxis to C5a.

DETAILED DESCRIPTION

Figure 1:
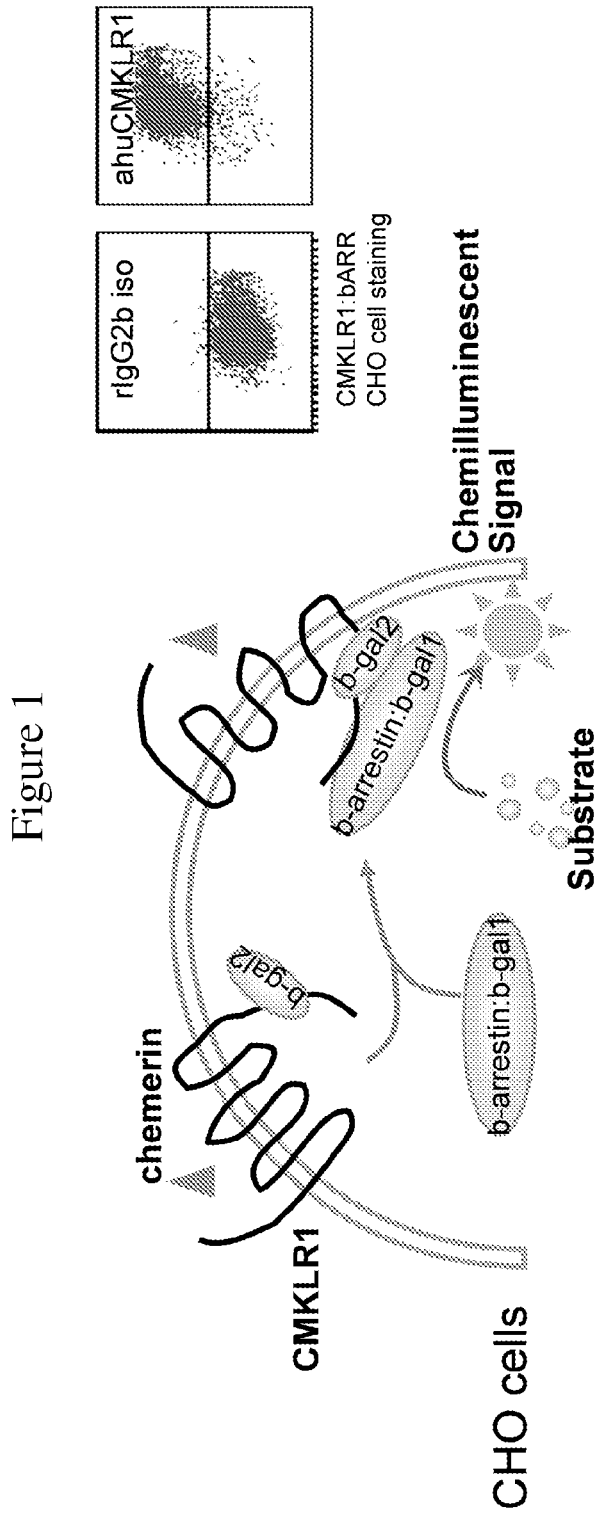
FIG. 1 shows a schematic of events in receptor internalization with ligand-triggered association with beta-arrestin2 and CMKLR1 expression by the CHO/bARR cell line used to screen compounds for CMKLR1 antagonists.

As summarized above, the present invention is drawn to methods for inhibiting the activity of CMKLR1. In some embodiments such methods include treating demyelinating inflammatory disease in a subject by administering an agent that antagonizes the activity of chemokine-like receptor 1 (CMKLR1) and/or a CMKLR1 ligand (e.g., chemerin or other endogenous CMKLR1 ligands. As such, the methods of the invention find use in treating EAE or MS in a subject. Methods of screening for agents that regulate demyelinating inflammatory disease are also provided.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

TERMS

"Activity" of CMKLR1 shall mean any signaling or binding function performed by that protein.

"Comparable cell" shall mean a cell whose type is identical to that of another cell to which it is compared. Examples of comparable cells are cells from the same cell line.

"Inhibiting" the onset of a disorder shall mean either lessening the likelihood of the disorder's onset, or preventing the onset of the disorder entirely. In the preferred embodiment, inhibiting the onset of a disorder means preventing its onset entirely. As used herein, onset may also refer to deterioration in a patient that has chronic/progressive disease, or relapse in a patient that has ongoing relapsing-remitting disease.

The methods of the invention may be specifically applied to individuals that have been diagnosed with an autoimmune disease, e.g. a chronic/progressive or relapsing-remitting disease such as MS or EAE. Treatment is aimed at the treatment or prevention of relapses, which are an exacerbation of a pre-existing condition.

"Inhibiting" the expression of a gene in a cell shall mean either lessening the degree to which the gene is expressed, or preventing such expression entirely.

"Specifically inhibit" the expression of a protein shall mean to inhibit that protein's expression or activity (a) more than the expression or activity of any other protein, or (b) more than the expression or activity of all but 10 or fewer other proteins.

"Subject" or "patient" shall mean any animal, such as a human, non-human primate, mouse, rat, guinea pig or rabbit.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

"Treating" a disorder shall mean slowing, stopping or reversing the disorder's progression. In the preferred embodiment, treating a disorder means reversing the disorder's progression, ideally to the point of eliminating the disorder itself. As used herein, ameliorating a disorder and treating a disorder are equivalent.

The term "immune" response is the development of a beneficial humoral (antibody mediated) and/or a cellular (mediated by antigen-specific T cells or their secretion products) response directed against CMKLR1 in a recipient patient. Such a response can be an active response induced by an "immunogen" that is capable of inducing an immunological response against itself on administration to a mammal, optionally in conjunction with an adjuvant.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R'' may be the same or different and are chosen from hydrogen, optionally substituted alkyl, cycloalkyl, alkenyl, cycloalkenyl, alkynyl, aryl, heteroaryl and heterocyclic.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen."

"Carboxyl," "carboxy" or "carboxylate" refers to —CO$_2$H or salts thereof.

"Carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Halo" or "halogen" refers to fluoro, chloro, bromo, and iodo.

"Hydroxy" or "hydroxyl" refers to the group —OH.

"Nitro" refers to the group —NO$_2$.

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Thiol" refers to the group —SH.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR⁷⁰, —SR⁷⁰, —NR⁸⁰R⁸⁰, trihalomethyl, —CN, —OCN, —SCN, —NO, —NO₂, =N₂, —N₃, —SO₂R⁷⁰, —SO₂O⁻M⁺, —SO₂OR⁷⁰, —OSO₂R⁷⁰, —OSO₂O⁻M⁺, —OSO₂OR⁷⁰, —P(O)(O⁻)₂(M⁺)₂, —P(O)(OR⁷⁰)O⁻M⁺, —P(O)(OR⁷⁰)₂, —C(O)R⁷⁰, —C(S)R⁷⁰, —C(NR⁷⁰)R⁷⁰, —C(O)O⁻M⁺, —C(O)OR⁷⁰, —C(S)OR⁷⁰, —C(O)NR⁸⁰R⁸⁰, —C(NR⁷⁰)NR⁸⁰R⁸⁰, —OC(O)R⁷⁰, —OC(S)R⁷⁰, —OC(O)O⁻M⁺, —OC(O)OR⁷⁰, —OC(S)OR⁷⁰, —NR⁷⁰C(O)R⁷⁰, —NR⁷⁰C(S)R⁷⁰, —NR⁷⁰CO₂⁻M⁺, —NR⁷⁰CO₂R⁷⁰, —NR⁷⁰C(S)OR⁷⁰, —NR⁷⁰C(O)NR⁸⁰R⁸⁰, —NR⁷⁰C(NR⁷⁰)R⁷⁰ and —NR⁷⁰C(NR⁷⁰)NR⁸⁰R⁸⁰, where R⁶⁰ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R⁷⁰ is independently hydrogen or R⁶⁰; each R⁸⁰ is independently R⁷⁰ or alternatively, two R^λ's, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each M⁺ is a counter ion with a net single positive charge. Each M⁺ may independently be, for example, an alkali ion, such as K⁺, Na⁺, Li⁺; an ammonium ion, such as ⁺N(R⁶⁰)₄; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR⁸⁰R⁸⁰ is meant to include —NH₂, —NH-alkyl, N-pyrrolidinyl, N-piperazinyl, 4N-methyl-piperazin-1-yl and N-morpholinyl.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

Representative Embodiments

The present invention provides methods for treating autoimmune disease, including inflammatory demyelinating diseases, such multiple sclerosis; etc. These methods comprise administering to the subject having an autoimmune condition, e.g. a demyelinating condition; an effective amount of an inhibitor of CMKLR1.

In some embodiments, a method is provided for inhibiting autoimmune diseases in a subject, the method comprising administering to the subject a prophylactically effective amount of a small molecule that specifically reduces levels of CMKLR1. In other embodiments, a method is provided for inhibiting inflammatory demyelinating disease in a subject, the method comprising administering to the subject a therapeutically effective amount of a small molecule.

In other embodiments, the method comprising administering to said subject an agent that downregulates the expression, or inhibits the activity of, a ligand of CMKLR1, which ligand includes, without limitation, chemerin. In these methods, the CMKLR1-expressing cell can be, without limitation, a macrophage; a dendritic cell; or a microglial cell.

Small Molecule Compounds

This disclosure concerns compounds which are useful as small molecule CMKLR1 antagonists in demyelinating disease and are thus useful for treating a variety of diseases and disorders that are mediated or sustained through the activity of CMKLR1. This disclosure also relates to pharmaceutical compositions comprising these compounds, methods of using these compounds in the treatment of various diseases and disorders, processes for preparing these compounds and intermediates useful in these processes.

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The present embodiments provide a compound of formula (I):

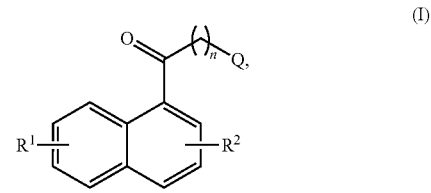

wherein
Q is selected from —NR$^Q$₄⁺, —NH₄⁺, —NH₂, —NHR$^Q$, —NR$^Q$₂, —OH, —SH, and lower alkyl; wherein R$^Q$ is lower alkyl; and wherein; Q is selected from —NR$^Q$₄⁺ or —NH₄⁺, then X⁻ is present and is a counterion;
R¹ and R² are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, and sulfonyl; and n is a number from one to four.

In formula (I), Q is selected from —$NR^Q_4{}^+$, —$NH_4{}^+$, —$NH_2$, —$NHR^Q$, —$NR^Q_2$, —OH, —SH, and lower alkyl; wherein $R^Q$ is lower alkyl; and wherein; Q is selected from —$NR^Q_4{}^+$ or —$NH_4{}^+$, then $X^-$ is present and is a counterion;

In certain embodiments, Q is —$NR^Q_4{}^+$, wherein $R^Q$ is lower alkyl; and wherein $X^-$ is present and is a counterion. In certain embodiments, $X^-$ is selected from fluoride, bromide, chloride, and fluoride.

In certain embodiments, Q is selected from —$NR^Q_4{}^+$ and —$NH_4{}^+$, wherein $R^Q$ is lower alkyl; and wherein $X^-$ is present and is a counterion. In certain embodiments, $X^-$ is selected from fluoride, bromide, chloride, and fluoride.

In certain embodiments, Q is selected from —$NH_2$, —$NHR^Q$, and —$NR^Q_2$; wherein $R^Q$ is lower alkyl. In certain embodiments, Q is —$NH_2$. In certain embodiments, Q is —$NHR^Q$; wherein $R^Q$ is lower alkyl. In certain embodiments, Q is —$NR^Q_2$; wherein $R^Q$ is lower alkyl.

In certain embodiments, Q is selected from —OH, —SH, and lower alkyl. In certain embodiments, Q is —OH. In certain embodiments, Q is —SH. In certain embodiments, Q is lower alkyl.

In formula (I), $R^1$ and $R^2$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, and sulfonyl.

In certain embodiments, $R^1$ and $R^2$ are hydrogen.

In certain embodiments, $R^1$ and $R^2$ are independently selected from hydrogen, alkyl, and substituted alkyl. In certain embodiments, $R^1$ and $R^2$ are independently selected from hydrogen, hydroxy, alkoxy, and substituted alkoxy. In certain embodiments, $R^1$ and $R^2$ are independently selected from hydrogen, amino, and substituted amino. In certain embodiments, $R^1$ and $R^2$ are independently selected from hydrogen, carboxyl, and carboxyl ester. In certain embodiments, $R^1$ and $R^2$ are independently selected from hydrogen, cyano, halogen, acyl, aminoacyl, nitro, and sulfonyl.

In formula (I), n is a number from one to four. In certain embodiments, n is one. In certain embodiments, n is two. In certain embodiments, n is three. In certain embodiments, n is four.

The present embodiments provide a compound of formula (II):

$$\text{(II)}$$

wherein

Q is selected from —$NR^Q_4{}^+$, —$NH_4{}^+$, —$NH_2$, —$NHR^Q$, —$NR^Q_2$, —OH, —SH, and lower alkyl; wherein $R^Q$ is lower alkyl; and wherein; Q is selected from —$NR^Q_4{}^+$ or —$NH_4{}^+$, then $X^-$ is present and is a counterion; and n is a number from one to four.

In formula (II), Q is selected from —$NR^Q_4{}^+$, —$NH_4{}^+$, —$NH_2$, —$NHR^Q$, —$NR^Q_2$, —OH, —SH, and lower alkyl; wherein $R^Q$ is lower alkyl; and wherein; Q is selected from —$NR^Q_4{}^+$ or —$NH_4{}^+$, then $X^-$ is present and is a counterion.

In certain embodiments, Q is —$NR^Q_4{}^+$, wherein $R^Q$ is lower alkyl; and wherein $X^-$ is present and is a counterion. In certain embodiments, $X^-$ is selected from fluoride, bromide, chloride, and fluoride.

In certain embodiments, Q is selected from —$NR^Q_4{}^+$ and —$NH_4{}^+$, wherein $R^Q$ is lower alkyl; and wherein $X^-$ is present and is a counterion. In certain embodiments, $X^-$ is selected from fluoride, bromide, chloride, and fluoride.

In certain embodiments, Q is selected from —$NH_2$, —$NHR^Q$, and —$NR^Q_2$; wherein $R^Q$ is lower alkyl. In certain embodiments, Q is —$NH_2$. In certain embodiments, Q is —$NHR^Q$; wherein $R^Q$ is lower alkyl. In certain embodiments, Q is —$NR^Q_2$; wherein $R^Q$ is lower alkyl.

In certain embodiments, Q is selected from —OH, —SH, and lower alkyl. In certain embodiments, Q is —OH. In certain embodiments, Q is —SH. In certain embodiments, Q is lower alkyl.

In formula (II), n is a number from one to four. In certain embodiments, n is one. In certain embodiments, n is two. In certain embodiments, n is three. In certain embodiments, n is four.

The present embodiments provide a compound of formula (III):

$$\text{(III)}$$

wherein

Q is selected from —$NR^Q_4{}^+$, —$NH_4{}^+$, —$NH_2$, —$NHR^Q$, —$NR^Q_2$, —OH, —SH, and lower alkyl; wherein $R^Q$ is lower alkyl; and wherein; Q is selected from —$NR^Q_4{}^+$ or —$NH_4{}^+$, then $X^-$ is present and is a counterion.

In formula (III), Q is selected from —$NR^Q_4{}^+$, —$NH_4{}^+$, —$NH_2$, —$NHR^Q$, —$NR^Q_2$, —OH, —SH, and lower alkyl; wherein $R^Q$ is lower alkyl; and wherein; Q is selected from —$NR^Q_4{}^+$ or —$NH_4{}^+$, then $X^-$ is present and is a counterion;

In certain embodiments, Q is —$NR^Q_4{}^+$, wherein $R^Q$ is lower alkyl; and wherein $X^-$ is present and is a counterion. In certain embodiments, $X^-$ is selected from fluoride, bromide, chloride, and fluoride.

In certain embodiments, Q is selected from —$NR^Q_4{}^+$ and —$NH_4{}^+$, wherein $R^Q$ is lower alkyl; and wherein $X^-$ is present and is a counterion. In certain embodiments, $X^-$ is selected from fluoride, bromide, chloride, and fluoride.

In certain embodiments, Q is selected from —$NH_2$, —$NHR^Q$, and —$NR^Q_2$; wherein $R^Q$ is lower alkyl. In certain embodiments, Q is —$NH_2$. In certain embodiments, Q is —$NHR^Q$; wherein $R^Q$ is lower alkyl. In certain embodiments, Q is —$NR^Q_2$; wherein $R^Q$ is lower alkyl.

In certain embodiments, Q is selected from —OH, —SH, and lower alkyl. In certain embodiments, Q is —OH. In certain embodiments, Q is —SH. In certain embodiments, Q is lower alkyl.

A particular compound of interest is shown as Formula IV below:

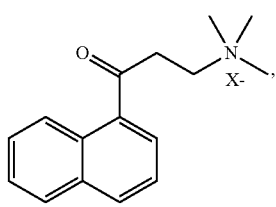

(IV)

wherein
X⁻ is selected from iodide, bromide, chloride, and fluoride.
A particular compound of interest is 2-(alpha-naphthoyl)ethyltrimethyl ammonium iodide, shown below:

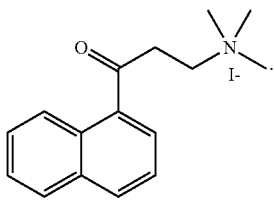

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Exemplary synthetic methods for the compounds described herein are described below.

In certain embodiments, 2-(alpha-naphthoyl)ethyltrimethyl ammonium iodide, shown below:

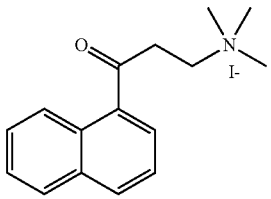

is commercially available. In certain embodiments, counterion exchanges can be performed with ion exchange chromatography. Modification of the naphthyl ring with substituents can be performed with standard chemical reactions known to one skilled in the art. Suitable reactions for modification of the naphthyl ring include electrophilic aromatic substitution. For example, the naphthyl ring can react with chlorine to form a chloro-substituted naphthyl ring. Further reaction of chloro-substituted naphthyl ring can occur with appropriate substituents. The naphthyl ring can also be alkylated using Friedel-Crafts reactions.

In certain embodiments, a Friedel-Crafts acylation can be performed on naphthylene. Further reaction of carbonyl group of the acylated naphthyl ring can be performed to obtain compounds of Formula (I)-(III).

Administration

In a certain embodiment, the present invention is drawn to methods for treating demyelinating inflammatory disease in a subject by administering an agent that antagonizes the activity of chemokine-like receptor 1 (CMKLR1) and/or a CMKLR1 ligand (e.g., chemerin or other endogenous CMKLR1 ligands).

In a certain embodiment, relapse of an autoimmune disease in a subject is inhibited or prevented by administering to the subject a prophylactically or therapeutically effective amount of an agent of the invention.

Determining a therapeutically or prophylactically effective amount of the CMKLR1 inhibitor compositions can be done based on animal data using routine computational methods.

In this invention, administering the instant compositions can be effected or performed using any of the various methods and delivery systems known to those skilled in the art. The administering can be performed, for example, intravenously, orally, via implant, transmucosally, transdermally, intramuscularly, intrathecally, and subcutaneously. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone. Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and Jun. 2, 2005 antioxidants (e.g., parabens, vitamins E and C, and ascorbic acid), anti-caking agents, coating agents, and chelating agents (e.g., EDTA), captisol, etc.

Conditions for Analysis and Therapy

The compositions and methods of the invention find use in combination with a variety of demyelinating autoimmune conditions, including chronic/progressive and relapsing demyelinating autoimmune diseases. Generally patients for the methods of the present invention are diagnosed as having an autoimmune condition, e.g. a relapsing-remitting autoimmune condition, prior to treatment. The inhibition of CMKLR1 decreases the severity or incidence of relapses in such patients.

Multiple sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

Clinical data alone may be sufficient for a diagnosis of MS. If an individual has suffered two separate episodes of neurologic symptoms characteristic of MS, and the individual also has consistent abnormalities on physical examination, a diagnosis of MS can be made with no further testing. Magnetic resonance imaging (MRI) of the brain and spine is often used during the diagnostic process. MRI shows areas of demyelination (lesions) as bright spots on the image. A substance, called Gadolinium, can be injected into the spinal column to highlight active plaques and, by elimination, demonstrate the existence of historical lesions not associated with clinical symptoms. This can provide the evidence of chronic disease needed for a definitive diagnosis of MS. Testing of cerebrospinal fluid (CSF) can provide evidence of chronic inflammation of the central nervous system. The CSF is tested for oligoclonal bands, which are immunoglobulins found in 85% to 95% of people with definite MS. Combined with MRI and clinical data, the presence of oligoclonal bands can help make a definite diagnosis of MS. Lumbar puncture is the procedure used to collect a sample of CSF.

The brain of a person with MS often responds less actively to stimulation of the optic nerve and sensory nerves. These brain responses can be examined using visual evoked potentials (VEPs) and somatosensory evoked potentials (SEPs). Decreased activity on either test can reveal demyelination which may be otherwise asymptomatic. Along with other data, these exams can help find the widespread nerve involvement required for a definite diagnosis of MS.

In 1996 the United States National Multiple Sclerosis Society standardized the following four subtype definitions (see Lublin and Reingold (1996) Neurology 46(4):907-11, herein specifically incorporated by reference) as relapsing-remitting; secondary progressive; primary progressive; progressive relapsing. The methods of the invention find particular use in the treatment of ongoing disease, and particularly in treating relapsing forms.

Relapsing-remitting describes the initial course of 85% to 90% of individuals with MS. This subtype is characterized by unpredictable attacks (relapses) followed by periods of months to years of relative quiet (remission) with no new signs of disease activity. Deficits suffered during the attacks may either resolve or may be permanent. When deficits always resolve between attacks, this is referred to as "benign" MS.

Secondary progressive describes around 80% of those with initial relapsing-remitting MS, who then begin to have neurologic decline between their acute attacks without any definite periods of remission. This decline may include new neurologic symptoms, worsening cognitive function, or other deficits. Secondary progressive is the most common type of MS and causes the greatest amount of disability.

Primary progressive describes the approximately 10% of individuals who never have remission after their initial MS symptoms. Decline occurs continuously without clear attacks. The primary progressive subtype tends to affect people who are older at disease onset.

Progressive relapsing describes those individuals who, from the onset of their MS, have a steady neurologic decline but also suffer superimposed attacks; and is the least common of all subtypes.

Peripheral neuropathies may also have a relapsing remitting course, and may include Miller Fisher syndrome; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy; IgM monoclonal gammopathies with its subtypes Waldenstrom's macroglobulinemia, myelin-associated glycoprotein-associated gammopathy, polyneuropathy, organomegaly, endocrinopathy, M-protein, skin changes syndrome, mixed cryoglobulinemia, gait ataxia, late-onset polyneuropathy syndrome, and MGUS.

An inhibitory agent may inhibit the activity of CMKLR1 by a variety of different mechanisms. In certain embodiments, the inhibitory agent is one that binds to the protein CMKLR1 and, in doing so, inhibits its activity. In other embodiments, the inhibitory agent prevents expression of CMKLR1.

An inhibitory agent may act on CMKLR1 mRNA to inhibit the activity of the target CMKLR1 by reducing the amount of CMKLR1 RNA present in the targeted cells, where the target cell may be present in vitro or in vivo. By "reducing the amount of" is meant that the level or quantity of the target CMKLR1 in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods. An effective dose of inhibitor can be the dose that provides for such a reduction in CMKLR1 activity.

Methods of Screening for CMKLR1 Antagonists

Agents that can regulate demyelinating inflammatory disease in a subject can be identified by detecting the ability of an agent to antagonize the activity of CMKLR1. Antagonizing agents include, but are not limited to, agents that interfere with the interaction of CMKLR1 with its natural ligands, agents that reduce CMKLR1 expression (e.g., by reducing transcription or by inducing cell surface receptor desensitization, internalization and/or degradation), agents that reduce expression of endogenous ligands of CMKLR1, and agents that inhibit intracellular signals initiated by the binding of CMKLR1 with its ligands. In some embodiments the screening methods are performed on analog or variants of 2-(alpha-naphthoyl)ethyltrimethylammonium iodide.

In certain embodiments, agents that can reduce demyelinating inflammatory disease in a subject can be identified by detecting the ability of an agent to interfere with (e.g., block) the interaction of CMKLR1 with its cognate ligand (e.g., chemerin). For example, a screening assay may be used that evaluates the ability of an agent to bind specifically to CMKLR1 (or its ligand) and prevent receptor:ligand interaction. Assays to determine affinity and specificity of binding are known in the art, including competitive and non-competitive assays. Assays of interest include ELISA, RIA, flow cytometry, etc. Binding assays may use purified or semi-purified protein, or alternatively may use primary cells or immortalized cell lines that express CMKLR1. In certain of these embodiments, the cells are transfected with an expression construct for CMKLR1. As an example of a binding assay, CMKLR1 is inserted into a membrane, e.g. whole cells, or membranes coating a substrate, e.g. microtiter plate, magnetic beads, etc. The candidate agent and soluble, labeled ligand (e.g., chemerin) are added to the cells, and the unbound components are then washed off. The ability of the agent to compete with the labeled ligand for receptor binding is determined by quantitation of bound, labeled ligand. Confirmation that the blocking agent does not cross-react with other chemoattractant receptors may be performed with a similar assay.

CMKLR1 protein sequences are used in screening of candidate compounds (including antibodies, peptides, lipids, small organic molecules, etc.) for the ability to bind to and modulate CMKLR1 activity. Agents that inhibit or reduce CMKLR1 activity are of interest as therapeutic agents for decreasing demyelinating inflammatory disease in a subject whereas agents that activate CMKLR1 activity are of interest as therapeutic agents for increasing demyelinating inflammatory disease in a subject. Such compound screening may be performed using an in vitro model, a genetically altered cell or animal, or purified protein corresponding to chemerin-like chemoattractant polypeptides or a fragment(s) thereof. One can identify ligands or substrates that bind to and modulate the action of the encoded polypeptide.

Polypeptides useful in screening include those encoded by the CMKLR1 gene, as well as nucleic acids that, by virtue of the degeneracy of the genetic code, are not identical in sequence to the disclosed nucleic acids, and variants thereof.

CMKLR1 ligands (e.g., chemerin or resolvin) may be used in screening of candidate compounds for the ability to bind to and modulate the ligands ability to activate CMKLR1. Agents that inhibit or reduce the ability of a CMKLR1 ligand to activate CMKLR1 are of interest as therapeutic agents for decreasing demyelinating inflammatory disease in a subject whereas agents that increase the ability of a CMKLR1 ligand to activate CMKLR1 activity are of interest as therapeutic agents for increasing demyelinating inflammatory disease in a subject. Such compound screening may be performed using an in vitro model, a genetically altered cell or animal, or purified protein corresponding to chemerin-like chemoattractant polypeptides or a fragment(s) thereof. One can identify ligands or substrates that bind to and modulate the action of the encoded polypeptide.

Polypeptides useful in screening include those encoded by a CMKLR1 ligand gene (e.g., chemerin), as well as nucleic acids that, by virtue of the degeneracy of the genetic code, are not identical in sequence to the disclosed nucleic acids, and variants thereof.

Transgenic animals or cells derived therefrom are also used in compound screening. Transgenic animals may be made through homologous recombination, where the normal locus corresponding to chemerin-like chemoattractant is altered. Alternatively, a nucleic acid construct is randomly integrated into the genome. Vectors for stable integration include plasmids, retroviruses and other animal viruses, yeast artificial chromosomes (YACs), and the like. A series of small deletions and/or substitutions may be made in the coding sequence to determine the role of different exons in receptor binding, signal transduction, etc. Specific constructs of interest include antisense sequences that block expression of the targeted gene and expression of dominant negative mutations. A detectable marker, such as lac Z or GFP, may be introduced into the locus of interest, where up-regulation of expression will result in an easily detected change in phenotype. One may also provide for expression of the target gene or variants thereof in cells or tissues where it is not normally expressed or at abnormal times of development, for example by overexpressing in neural cells. By providing expression of the target protein in cells in which it is not normally produced, one can induce changes in cell behavior.

Compound screening identifies agents that modulate CMKLR1 activity or function. Of particular interest are screening assays for agents that have a low toxicity for normal human cells. A wide variety of assays may be used for this purpose, including labeled in vitro protein-protein binding assays, electrophoretic mobility shift assays, immunoassays for protein binding, and the like. Screening for the activity of G-protein coupled receptors (or GPCRs, of which CMKLR1 is a member) is well known in the art, and includes assays for measuring any of a number of detectable steps, including but not limited to: stimulation of GDP for GTP exchange on a G protein; alteration of adenylate cyclase activity; protein kinase C modulation; phosphatidylinositol breakdown (generating second messengers diacylglycerol, and inositol triphosphate); intracellular calcium flux; activation of MAP kinases; modulation of tyrosine kinases; modulation of gene or reporter gene activity, integrin activation, or chemotaxis inhibition. A detectable step in a signaling cascade is considered modulated if the measurable activity is altered by 10% or more above or below a baseline or control level. The baseline or control level can be the activity in the substantial absence of an activator (e.g., a ligand) or the activity in the presence of a known amount of an activator. The measurable activity can be measured directly, as in, for example, measurement of cAMP or diacylglycerol levels. Alternatively, the measurable activity can be measured indirectly, as in, for example, a reporter gene assay. Knowledge of the 3-dimensional structure of the encoded protein (e.g., CMKLR1 or a ligand, e.g. chemerin), derived from crystallization of purified recombinant protein, could lead to the rational design of small drugs that specifically inhibit activity. These drugs may be directed at specific domains and sites.

The term "agent" as used herein describes any molecule, e.g. protein or pharmaceutical, with the capability of modulating the physiological function of CMKLR1 or its ligand. Generally a plurality of assay mixtures is run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, lipids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., *Pac. Symp. Biocompat.* 305-16, 1998); Sun et al., *J. Comput. Aided Mol. Des.* 12:597-604, 1998); each incorporated herein by reference in their entirety). For example, libraries of phosphatase inhibitors can be prepared by syntheses of combinatorial chemical libraries (see generally DeWitt et al., *Proc. Nat. Acad. Sci. USA* 90:6909-13, 1993; International Patent Publication WO 94/08051; Baum, *Chem. & Eng. News,* 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat. Acad. Sci. USA* 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 3 hours will be sufficient.

Preliminary screens can be conducted by screening for compounds capable of binding to CMKLR1 or its ligand; compounds so identified are possible modulators. Compounds capable of binding to CMKLR1 are inhibitors if they do not activate the receptor and activators if they do. The binding assays usually involve contacting CMKLR1 or its ligand with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89.

Certain screening methods involve screening for a compound that modulates the expression of CMKLR1 or its ligand. Such methods generally involve conducting cell-based assays in which test compounds are contacted with one or more cells endogenously expressing CMKLR1 or its ligand and then detecting a modulation in expression (e.g., at the mRNA and/or protein level). In certain screening methods, a target cell has a reporter gene (e.g., GFP) under the control of the CMKLR1 promoter (or promoter of its ligand). The level of expression can be compared to a baseline value. The baseline value can be a value for a control sample or a statistical value that is representative of expression levels for a control population. Expression levels can also be determined for cells that do not express the CMKLR1 or its ligand, as a negative control. Such cells generally are otherwise substantially genetically the same as the test cells. Various controls can be conducted to ensure that an observed activity is authentic including running parallel reactions with cells that lack the reporter construct or by not contacting a cell harboring the reporter construct with test compound.

Certain screening methods involve screening for a compound that modulates gene expression normally regulated by CMKLR1 signaling. In certain embodiments, a cell-based assay is conducted in which a cell expressing CMKLR1 is contacted to a candidate agent (e.g., a CMKLR1 binding agent) and monitored for changes in gene expression that are similar, or substantially similar, to those induced by a natural ligand for CMKLR1. In certain other embodiments, a cell-based assay is conducted in which a cell expressing CMKLR1 is contacted to its natural ligand and a candidate agent and monitored for perturbations in gene expression. By "perturbations in gene expression", it is meant that the gene expression changes induced by a CMKLR1 ligand binding to CMKLR1 is altered when the candidate agent is present.

Certain screening methods involve screening for a compound that modulates CMKLR1 signaling events when contacted to a cell expressing CMKLR1. These assays can be carried out in the presence or absence of a natural ligand for CMKLR1. Such methods generally involve monitoring for modulation of downstream signaling events as described above, e.g., protein phosphorylation, GDP/GTP exchange, etc. Including the b-ARR assay.

Compounds can also be further validated as described below.

Compounds that are initially identified by any of the foregoing screening methods can be further tested to validate their apparent activity. The basic format of such methods involves administering a lead compound identified during an initial screen to an animal that serves as a model for humans. The animal models utilized in validation studies generally are mammals. Specific examples of suitable animals include, but are not limited to, primates, mice, and rats.

Active test agents identified by the screening methods described herein that modulate CMKLR1 activity can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

A functional assay that detects leukocyte chemotaxis may be used for confirmation. For example, a population of cells that demonstrate chemerin chemotaxis (e.g., dendritic cells or monocyte/macrophages) may be stimulated with chemerin and/or the candidate modulating agent. An agent that antagonizes CMKLR1 activity will cause a decrease in the locomotion of the cells in response to chemerin. An agent that potentiates CMKLR1 activity will act as a chemotaxis factor in the absence of chemerin and/or increase the chemotactic response induced by chemerin. Chemotaxis assays of that find use in these methods are known in the art, examples of which are described in U.S. patent application Ser. No. 10/958,527, entitled "Family of Cystatin-Related Chemoattractant Proteins" (incorporated herein by reference in its entirety). An agent that is a chemoattractant inhibitor will decrease the concentration of cells at a target site of higher concentration of chemerin.

EXPERIMENTAL

Example 1

A small molecule CMKLR1 antagonist is identified as 2-(alpha-naphthoyl)ethyltrimethyl ammonium iodide (aN-ETA), shown below:

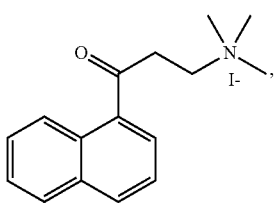

and has the following chemical formula: $C_{16}H_{20}HO^+$ (MW=242 Da, free base). aNETA inhibits chemerin mediated beta-arrestin2 association with CMKLR1 in an in vitro cell-based bioassay with an $IC_{50}$ of about 350 nM. In vivo, daily s.c. dosing with 10 mg of aNETA/kg mouse body weight for 8 days (followed by every other day dosing for the duration of the experiment) significantly delayed the onset of experimental autoimmune encephalomyelitis (EAE).

Example 2

Primary Screen: Inhibition of Chemerin-Triggered huCMKLR1 Association with Beta-Arrestin2

With reference to FIG. 1, early event in receptor internalization is ligand-triggered association with beta-arrestin2. This process turns off receptor signaling. Enzyme complementation can be used to measure CMKLR1 association with beta-arrestin2. In this assay β-Galactosidase is split into two complementary enzyme fragments, one is attached to CMKLR1, the other to beta-arrestin2. If ligand interaction with CMKLR1 promotes its association with β-arrestin2, the enzyme fragments join and become active.

An assay, such as PathHunter® CHO-K1 CMKLR1 β-Arrestin GPCR Assays (DiscoverX, Inc., Fremont, Calif.) can provide a method for monitoring activation of the CMKLR1 GPCR receptor through arrestin recruitment in live cells. CMKLR1 cells are engineered to co-express a ProLink (PK)-tagged GPCR and the Enzyme Acceptor (EA)-tagged β-Arrestin fusion proteins. Upon GPCR activation, the two enzyme fragments are brought together, forming an active β-Gal enzyme through Enzyme Fragment Complementation (EFC).

Example 3

Inhibition of Chemerin-Triggered huCMKLR1 Association with βARR by aNETA

Figure 2:
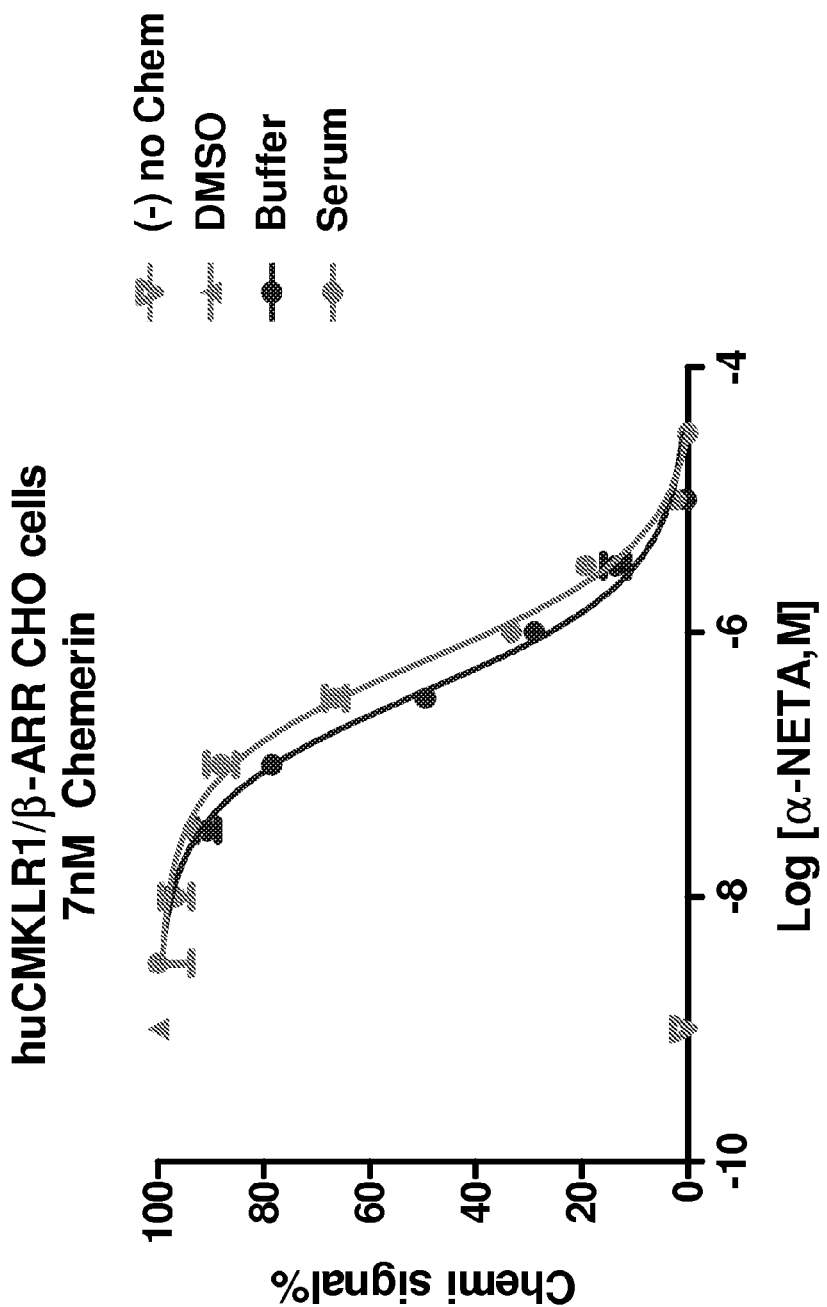
FIG. 2 shows a graph illustrating inhibition of chemerin-triggered huCMKLR1 association with βARR by aNETA.

A LOPAC (Library of Pharmacologically Active Compounds) library (Sigma-Aldrich, St. Louis, Mo.) was screened for inhibition of chemerin-triggered huCMKLR1 association with βARR. Three hits were obtained from a primary screen of LOPAC library. One hit was reproducible: 2-(alpha-naphthoyl)ethyltrimethyl ammonium iodide (aNETA). huCMKLR1/βARR CHO cells and 7 nM chemerin were used. The assay was performed in both buffer (10% FBS) or 100% human serum. The results from buffer and human serum for aNETA were of similar IC50s, as shown in FIG. 2. The IC50 result using buffer was 350 nM. The IC50 result using human serum was 620 nM.

Example 4

Figure 3:
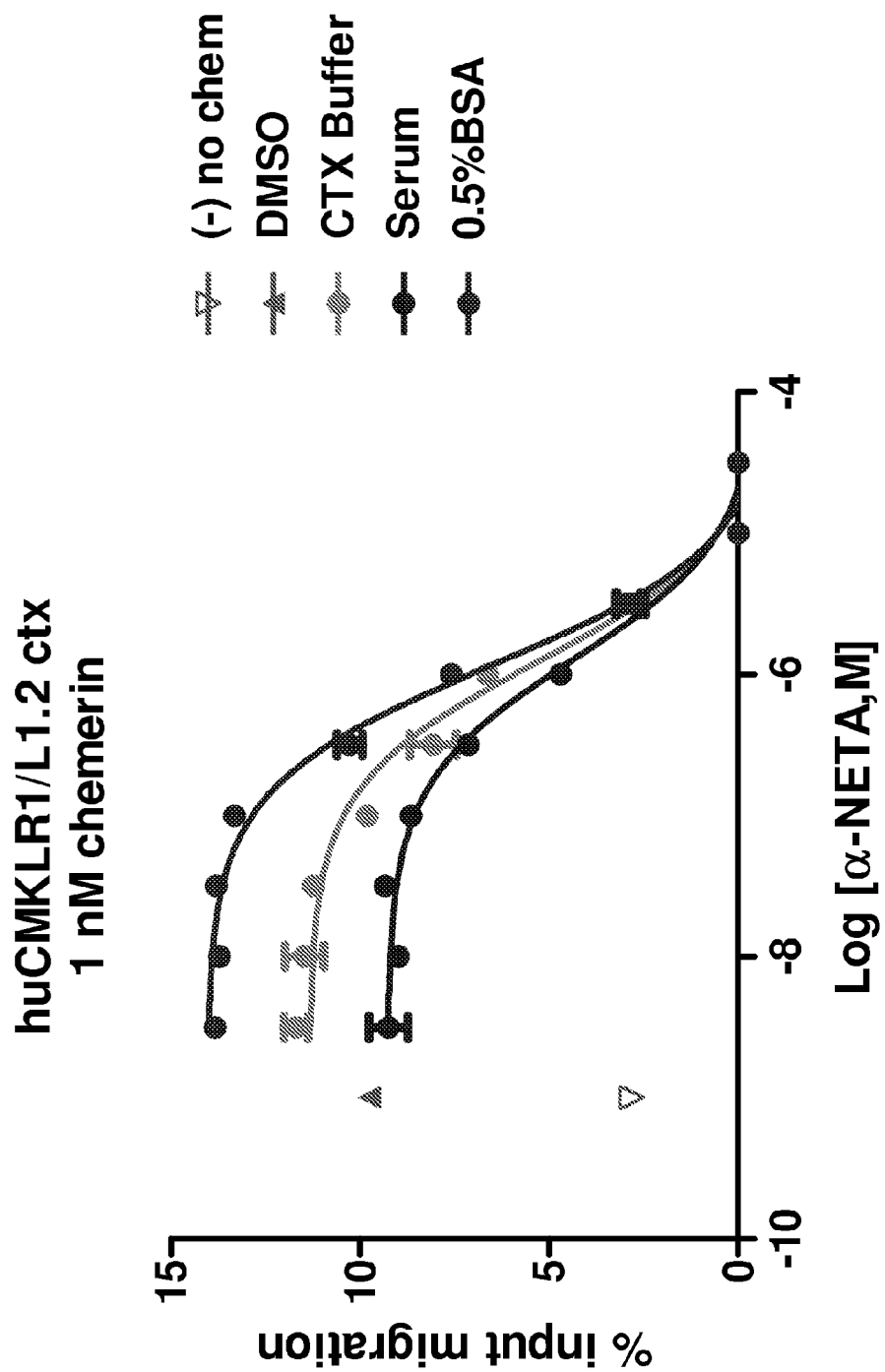
FIG. 3 shows a graph illustrating inhibition of chemerin-triggered human CMKLR1/L1.2 cell migration.

Inhibition of Chemerin-Triggered Human CMKLR1/L1.2 Cell Migration 2-(alpha-Naphthoyl)ethyltrimethyl ammonium iodide (aNETA) was tested for inhibition of chemerin-triggered human CMKLR1/L1.2 cell migration. huCMKLR1/L1.2 ctx and 1 nM chemerin were used. The assay was performed in 0.5% BSA, buffer (10% FBS), or 100% human serum. The results from 0.5% BSA, buffer (10% FBS), and 100% human serum were of similar IC50s, as shown in FIG. 3. The IC50 result using 0.5% BSA was 1.2 µM. The IC50 result using buffer was 1.2 µM. The IC50 result using human serum was 1.3 µM.

Example 5

Figure 4:
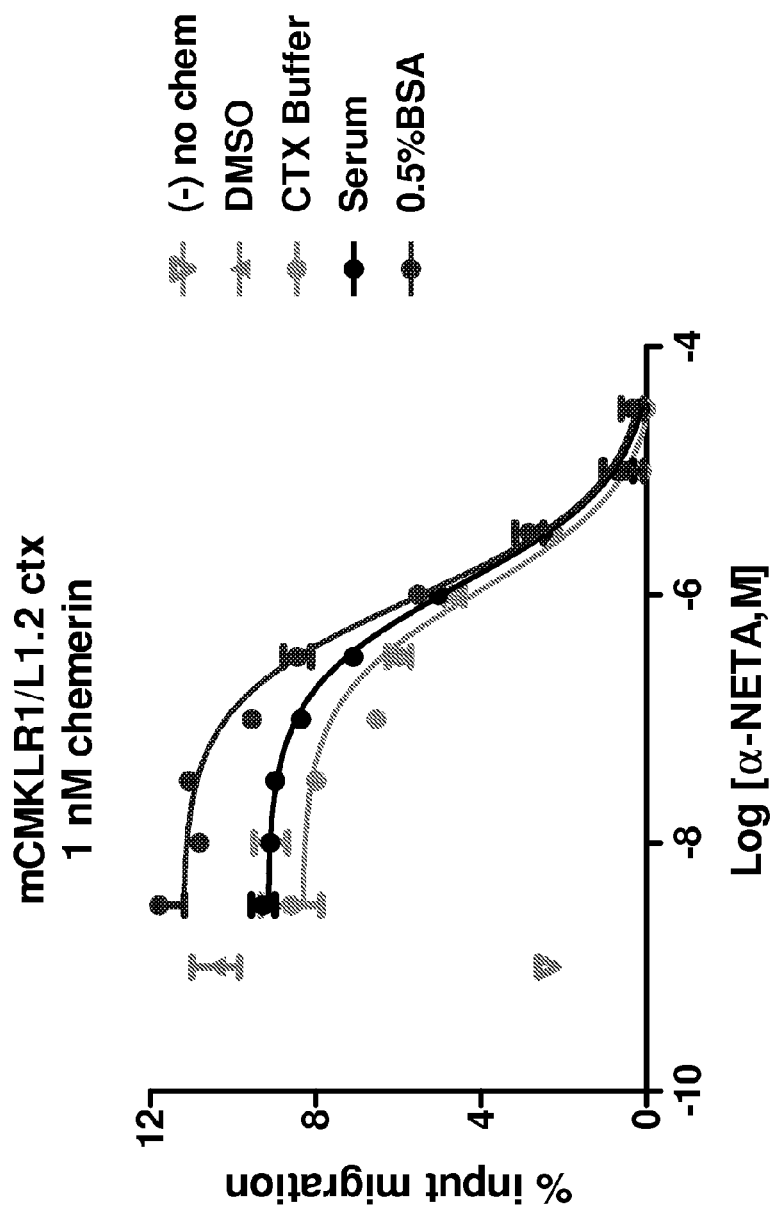
FIG. 4 shows a graph illustrating inhibition of chemerin-triggered mouse CMKLR1/L1.2 cell migration.

Inhibition of Chemerin-Triggered Mouse CMKLR1/L1.2 Cell Migration 2-(alpha-Naphthoyl)ethyltrimethyl ammonium iodide (aNETA) was tested for inhibition of chemerin-triggered mouse CMKLR1/L1.2 cell migration. mCMKLR1/L1.2 ctx and 1 nM chemerin were used. The assay was performed in 0.5% BSA, buffer (10% FBS), or 100% human serum. The results show that aNETA seems to cross to the mouse receptor. As shown in FIG. 4, the IC50 result using buffer was 1.1 µM. The IC50 result using human serum was 1.2 µM. The IC50 result using 0.5% BSA was 9.6 µM.

Example 6

Specificity: aNETA does not Inhibit CXCR4-Dependent MOLT-4 Migration to CXCL12

Figure 5:
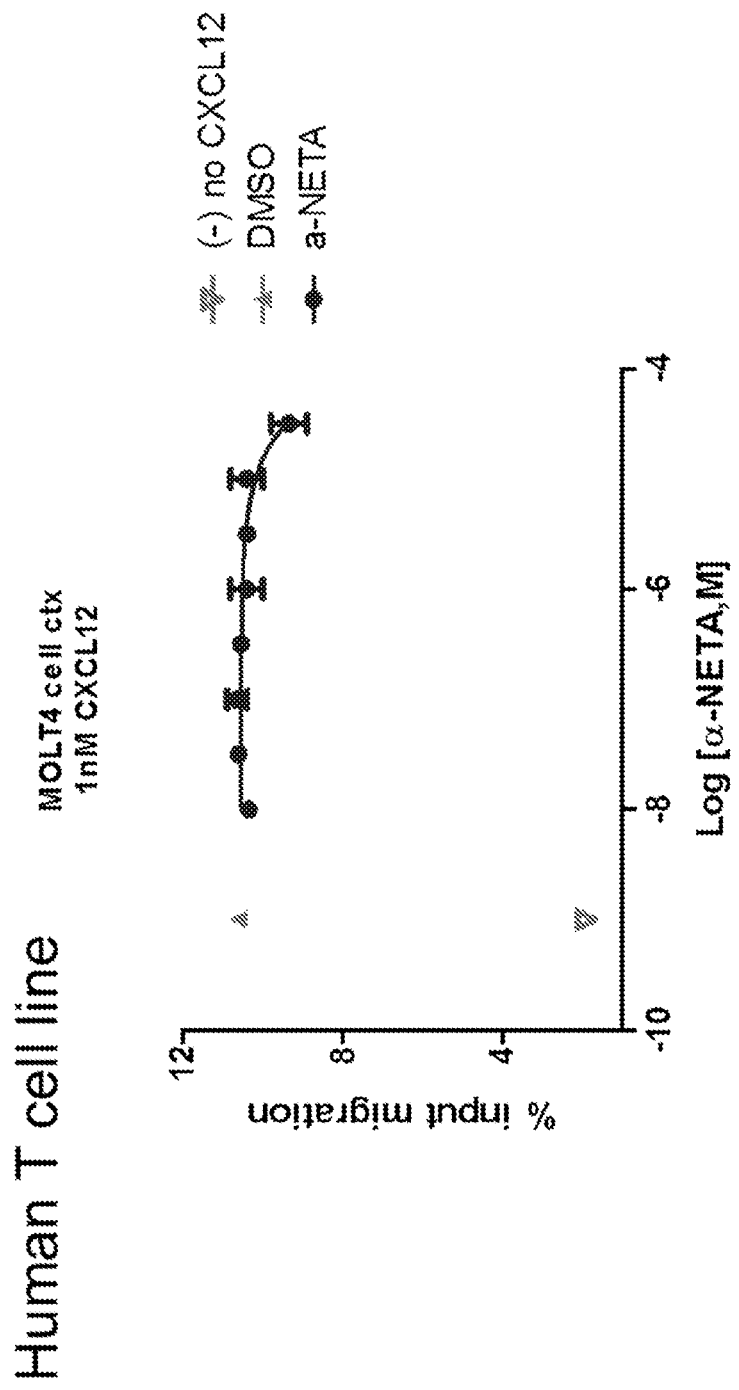
FIG. 5 shows a graph illustrating specificity in which aNETA does not inhibit CXCR4-dependent MOLT-4 migration to CXCL12.

MOLT4 cell ctx (human T-cell line) and 1 nM CXCL12 were used. As shown in FIG. 5, (alpha-Naphthoyl)ethyltrimethyl ammonium iodide (aNETA) was tested for inhibition of CXCR4-dependent MOLT-4 migration to CXCL12. aNETA does not inhibit CXCR4-dependent MOLT-4 migration to CXCL12.

Example 7

Specificity: aNETA does not Inhibit CCR9-Dependent MOLT-4 Migration to CCL25

Figure 6:
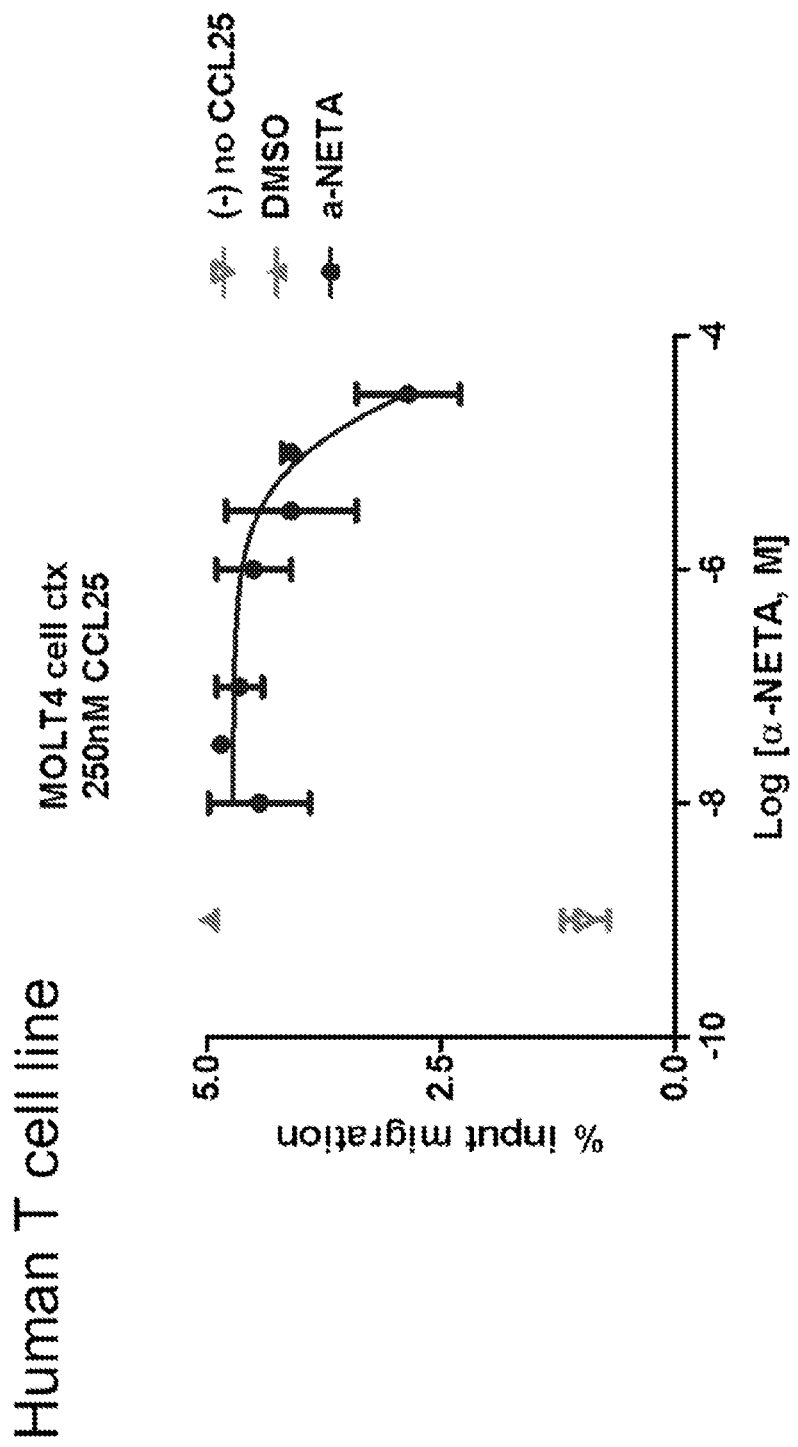
FIG. 6 shows a graph illustrating specificity in which aNETA does not inhibit CCR9-dependent MOLT-4 migration to CCL25.

MOLT4 cell ctx (human T-cell line) and 250 nM TECK were used. As shown in FIG. 6, (alpha-Naphthoyl)ethyltrimethyl ammonium iodide (aNETA) was tested for inhibition of CCR9-dependent MOLT-4 migration to CCL25. aNETA does not inhibit CCR9-dependent MOLT-4 migration to CCL25.

Example 8

Specificity: aNETA does not Inhibit CXCR4-Dependent Mouse Splenocyte Migration to CXCL12

Figure 7:
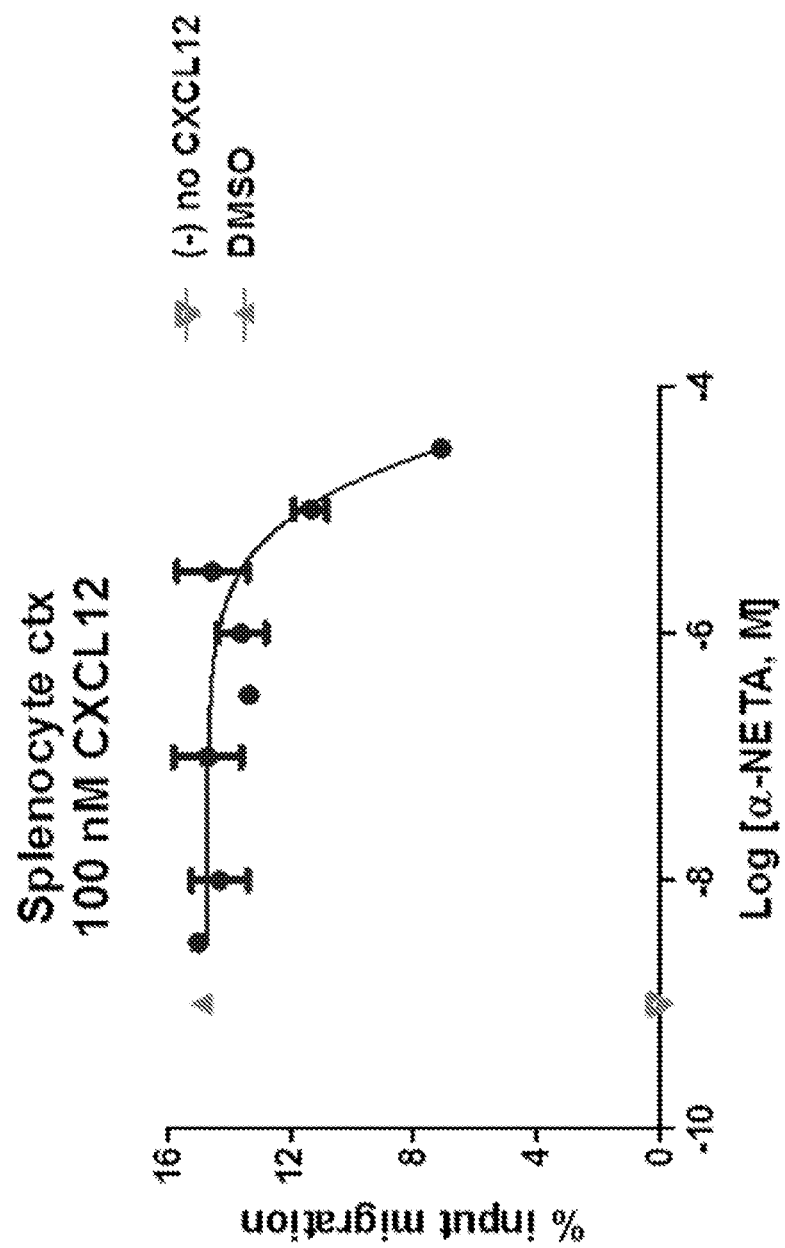
FIG. 7 shows a graph illustrating specificity in which aNETA does not inhibit CXCR4-dependent mouse splenocyte migration to CXCL12.

Splenocyte ctx and 100 nM CXCL12 were used. As shown in FIG. 7, (alpha-Naphthoyl)ethyltrimethyl ammonium iodide (aNETA) was tested for inhibition of CXCR4-dependent mouse splenocyte migration to CXCL12. aNETA does not inhibit CXCR4-dependent mouse splenocyte migration to CXCL12.

Example 9

Specificity: aNETA does not Inhibit CCR7-Dependent Mouse Splenocyte Migration to CCL19

Figure 8:
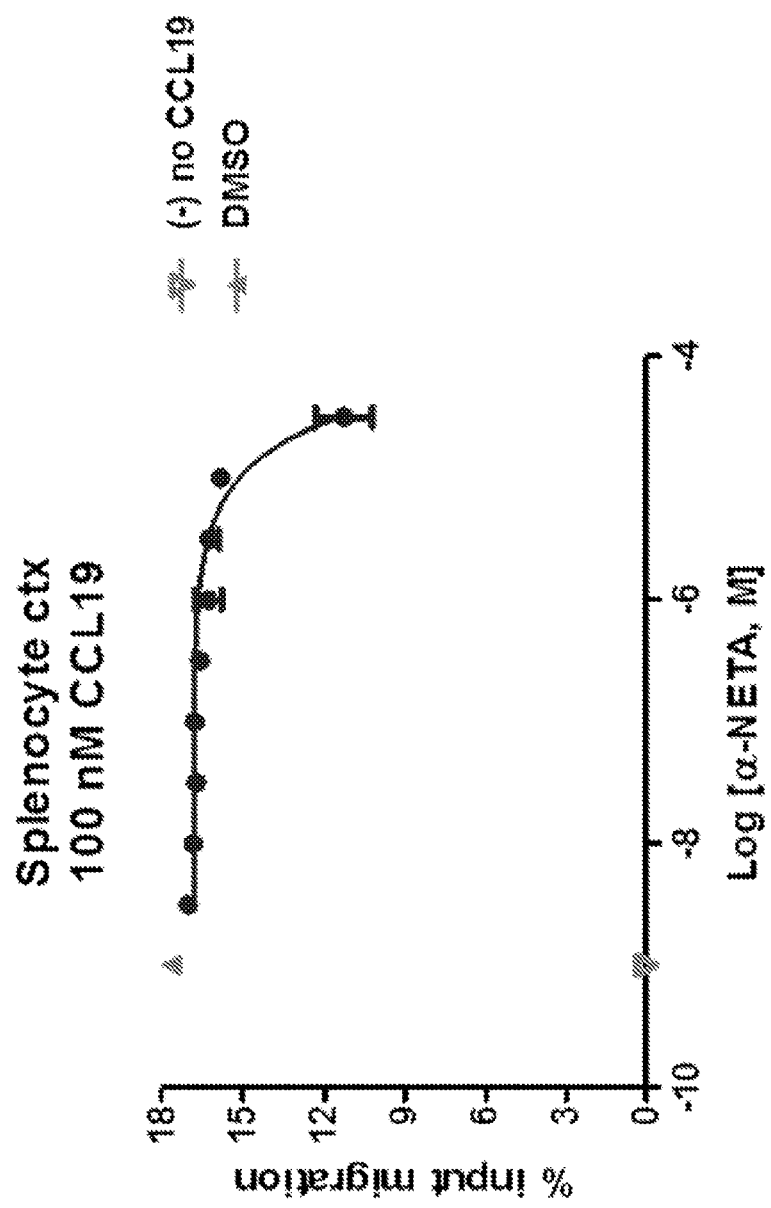
FIG. 8 shows a graph illustrating specificity in which aNETA does not inhibit CCR7-dependent mouse splenocyte migration to CCL19.

Splenocyte ctx and 100 nM CCL19 were used. As shown in FIG. 8, (alpha-Naphthoyl)ethyltrimethyl ammonium iodide (aNETA) was tested for inhibition of CCR7-dependent mouse splenocyte migration to CCL19. aNETA does not inhibit CCR7-dependent mouse splenocyte migration to CCL19.

Example 10

Figure 9:
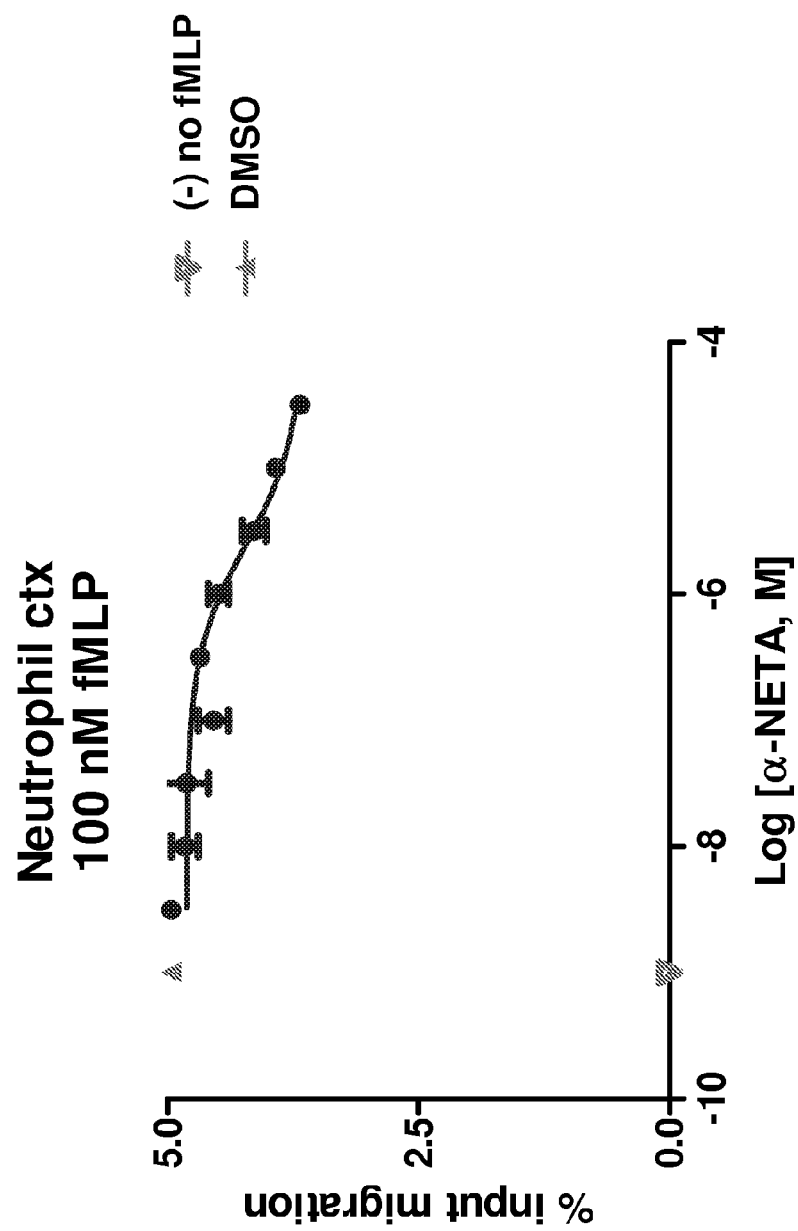
FIG. 9 shows a graph illustrating specificity in which aNETA does not inhibit FPR-dependent mouse BM neutrophil chemotaxis to fMLP.

Specificity: aNETA does not Inhibit FPR-Dependent Mouse BM Neutrophil Chemotaxis to fMLP Neutrophil ctx and 100 nM fMLP were used. As shown in FIG. 9, (alpha-Naphthoyl)ethyltrimethyl ammonium iodide (aNETA) was tested for inhibition of FPR-dependent mouse BM neutrophil chemotaxis to fMLP. aNETA does not inhibit FPR-dependent mouse BM neutrophil chemotaxis to fMLP.

Example 11

Figure 10:
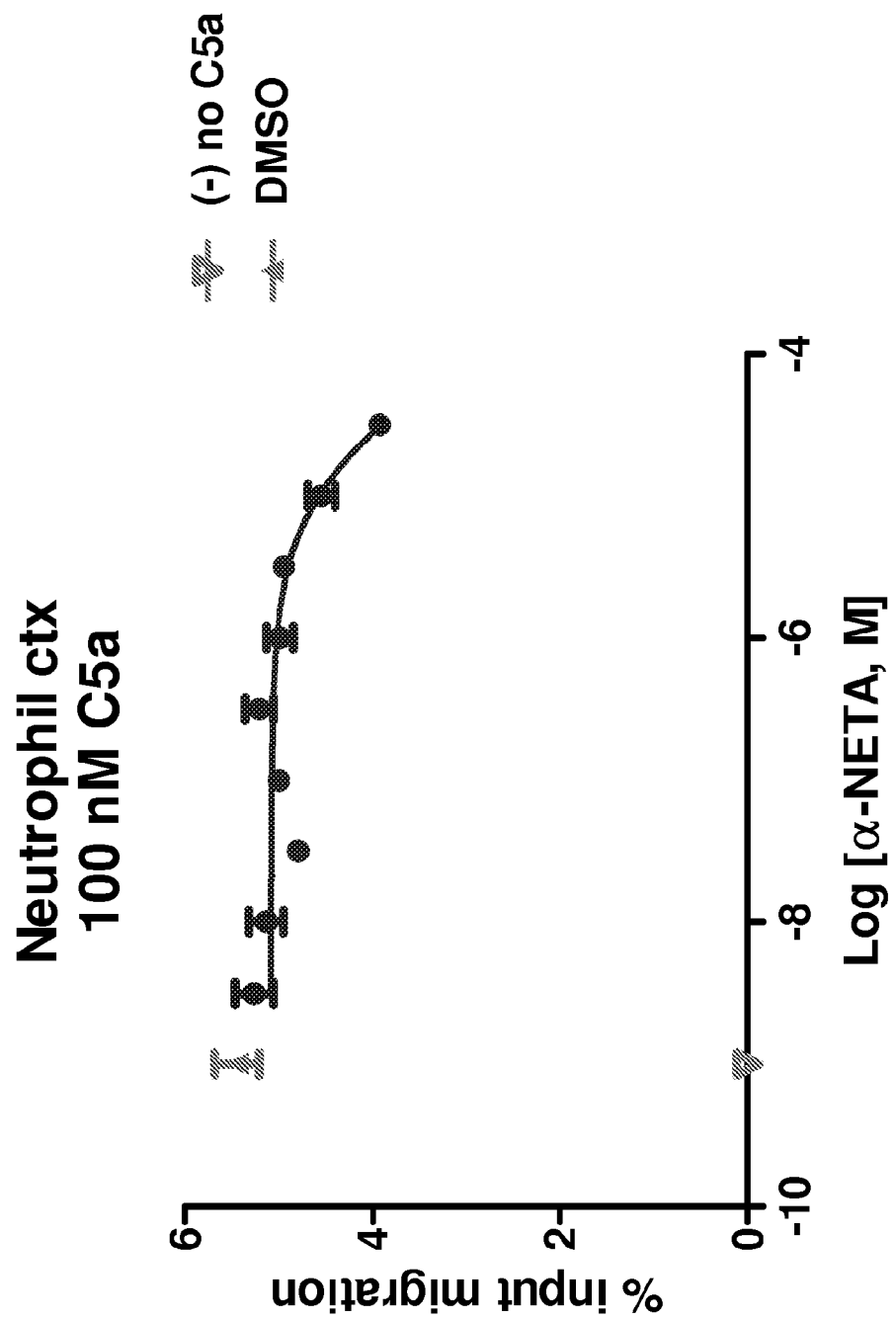

Specificity: aNETA does not Inhibit C5aR-Dependent Mouse BM Neutrophil Chemotaxis to C5a Neutrophil ctx and 100 nM C5a were used. As shown in FIG. 10, (alpha-Naphthoyl)ethyltrimethyl ammonium iodide (aNETA) was tested for inhibition of C5aR-dependent mouse BM neutrophil chemotaxis to C5a. aNETA does not inhibit C5aR-dependent mouse BM neutrophil chemotaxis to C5a.

Example 12 aNETA not Cytotoxic In Vitro

The in vitro cytotoxicity of aNETA can be determined with an annexin V FITC assay kit. One of the early hallmarks of early stage of apoptosis is that membrane phospholipids such as phosphatidylserine and phosphatidylethanolamine redistribute from the inner to outer leaflet of the membrane bilayer where they are exposed on the cell surface. Externalization of phosphatidylserine residues to the outer plasma membrane leaflet allows their detection via their high affinity for annexin V, a phospholipid binding protein. Apoptotic cells bound with fluorochrome-labeled annexin V can be visualized using fluorescence microscopy, flow cytometry, or a plate reader capable of fluorescence measurements. The analysis can be performed with a FITC-conjugated annexin-V, which has a strong affinity for extracellular phosphatidylserines, and the fluorescent intercalating agent propidium iodide (PI).

Figure 11:
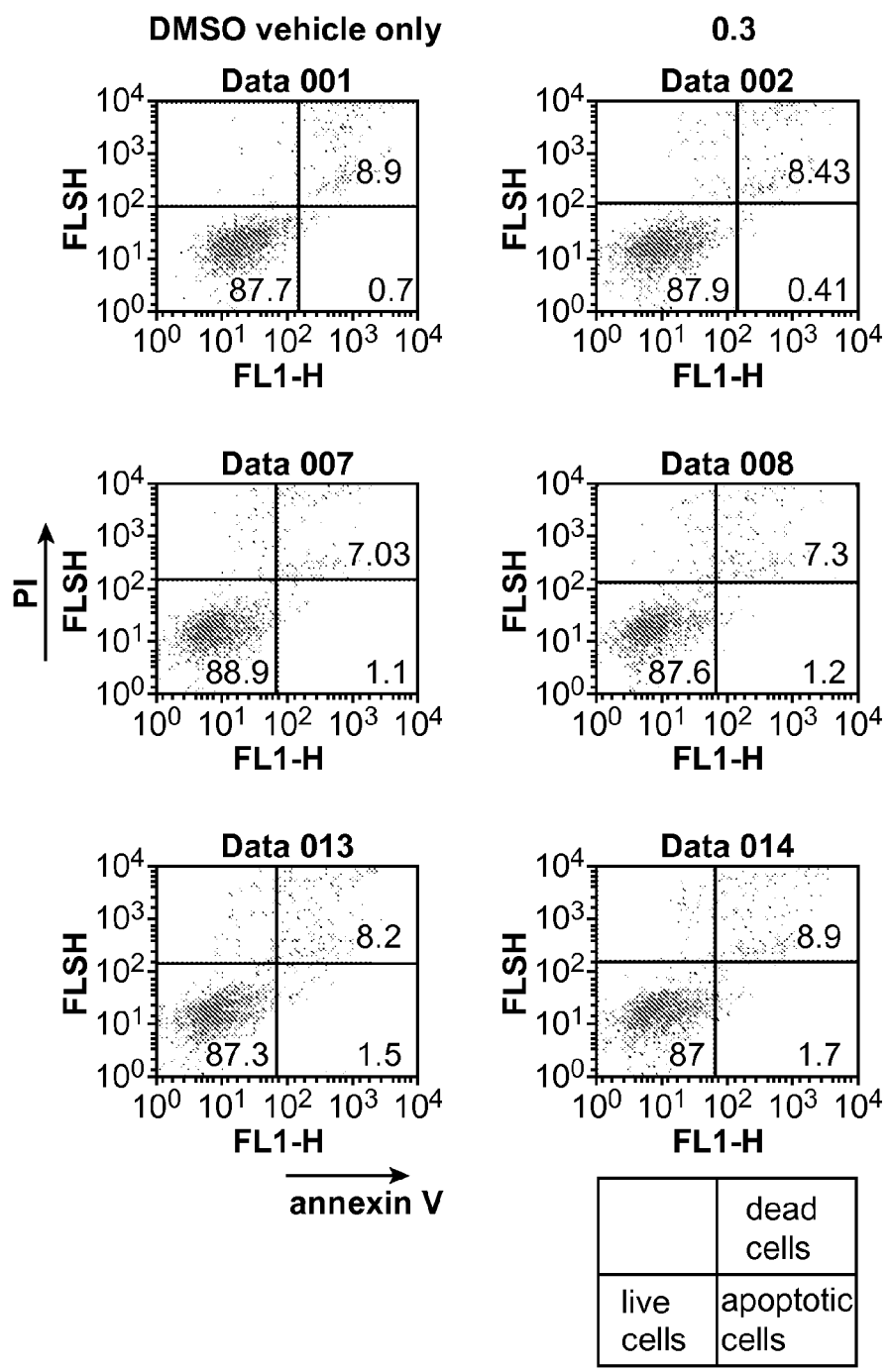
FIG. 11 shows graphs of cytotoxicity assay results of aNETA.

With reference to FIG. 11, cell lines (huCMKLR1/βARR CHO and huCMKLR1/L1.2) and splenocytes were used. aNETA was tested with 90 minute incubation at 37° C. Over the duration of the in vitro functional assays, aNETA does not appear to be acutely toxic.

Example 14 aNETA Suppresses Clinical EAE In Vivo

EAE was previously examined in CMKLR1 null mice immunized with MOG 35-55 in CFA (see, for example, U.S. Pat. No. 8,038,992, herein specifically incorporated by reference). These mice are resistant to the development of EAE relative to wild-type mice. EAE is driven by pathogenic immune responses against myelin proteins and lipids. CMKLR1 may have an inflammatory role. We next asked whether treatment with agents that inhibit CMKLR1, including aNETA, prevent and/or improve clinical EAE. To test this, WT mice with EAE are treated with aNETA.

Methods
EAE Induction.
EAE is induced in 8-12 week old female null and WT animals via subcutaneous immunization with 100 μg myelin oligodendrocyte glycoprotein) peptide, amino acids 35-55 (MOG 35-55) in an emulsion mixed (volume ratio 1:1) with Complete Freund's Adjuvant (containing 4 mg/ml of heat-killed *Mycobacterium tuberculosis* H37Ra). Mice are also injected intravenously with 250-400 ng of *Bordetella pertussis* toxin (BPT) in PBS at the time of, and two days following immunization. MOG 35-55 peptide is synthesized by the Stanford Protein and Nucleic Acid Facility and purified by high performance liquid chromatography (HPLC). Mice (n=8-10 per group) were examined daily for clinical signs of EAE and were scored as followed: 0=no clinical disease, 1=limp tail, 2=hindlimb weakness, 3=complete hindlimb paralysis, 4=hindlimb paralysis plus some forelimb paralysis, and 5=moribund or dead.

Histopathology.
Brains and spinal cords are dissected from mice, fixed in 10% formalin in PBS and embedded in paraffin. Seven micron thick sections are stained with haematoxylin and eosin to detect inflammatory infiltrates and luxol fast blue for demyelination. Inflammatory lesions in brain, thoracic and lumbar spinal cord sections are counted by an examiner masked to the treatment status of the animal.

Drug Dosing.
WT mice are induced with EAE using MOG 35-55 and pertussis toxin. aNETA is administered on the day of EAE induction in a 10% captisol formulation at 1,3, or 10 mg/kg (subcutaneous injection) and every day thereafter for 8 days, and then every other day until the conclusion of the study.

Figure 12:
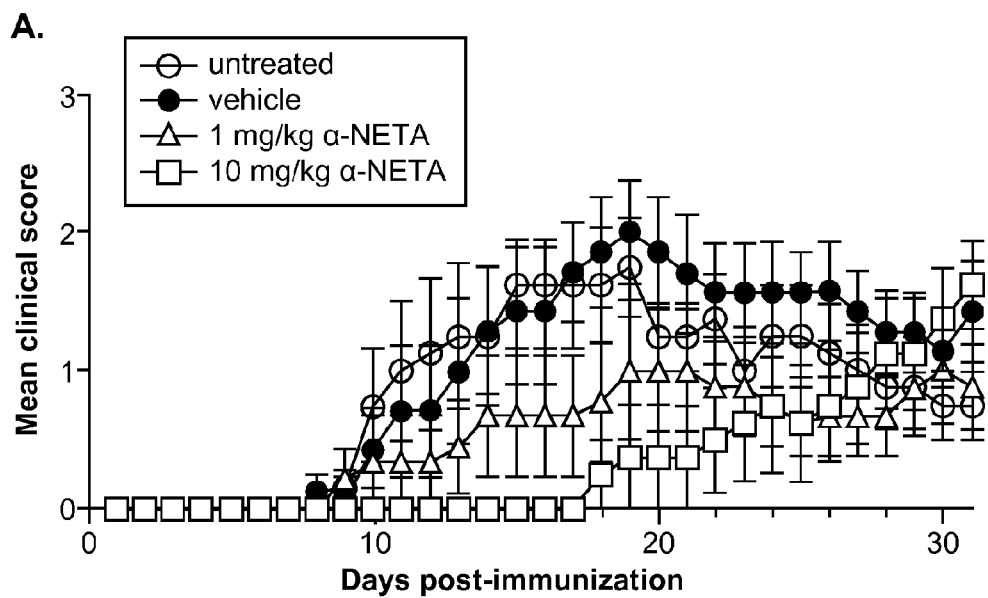
FIG. 12 shows a graph illustrating the result of administration of two different doses of aNETA and controls and the onset of EAE in days post-administration.

Results
aNETA suppresses clinical EAE in vivo. With reference to FIG. 12, daily administration of 1 mg/kg of aNETA resulted in onset of EAE of 17.8 days post-immunization. Daily administration of 10 mg/kg of aNETA resulted in onset of EAE of 26 days post-immunization. In comparison, untreated mice resulted in onset of EAE of 12.7 days post-immunization. Administration of vehicle resulted in onset of EAE of 13.3 days post-immunization.

Figure 13:
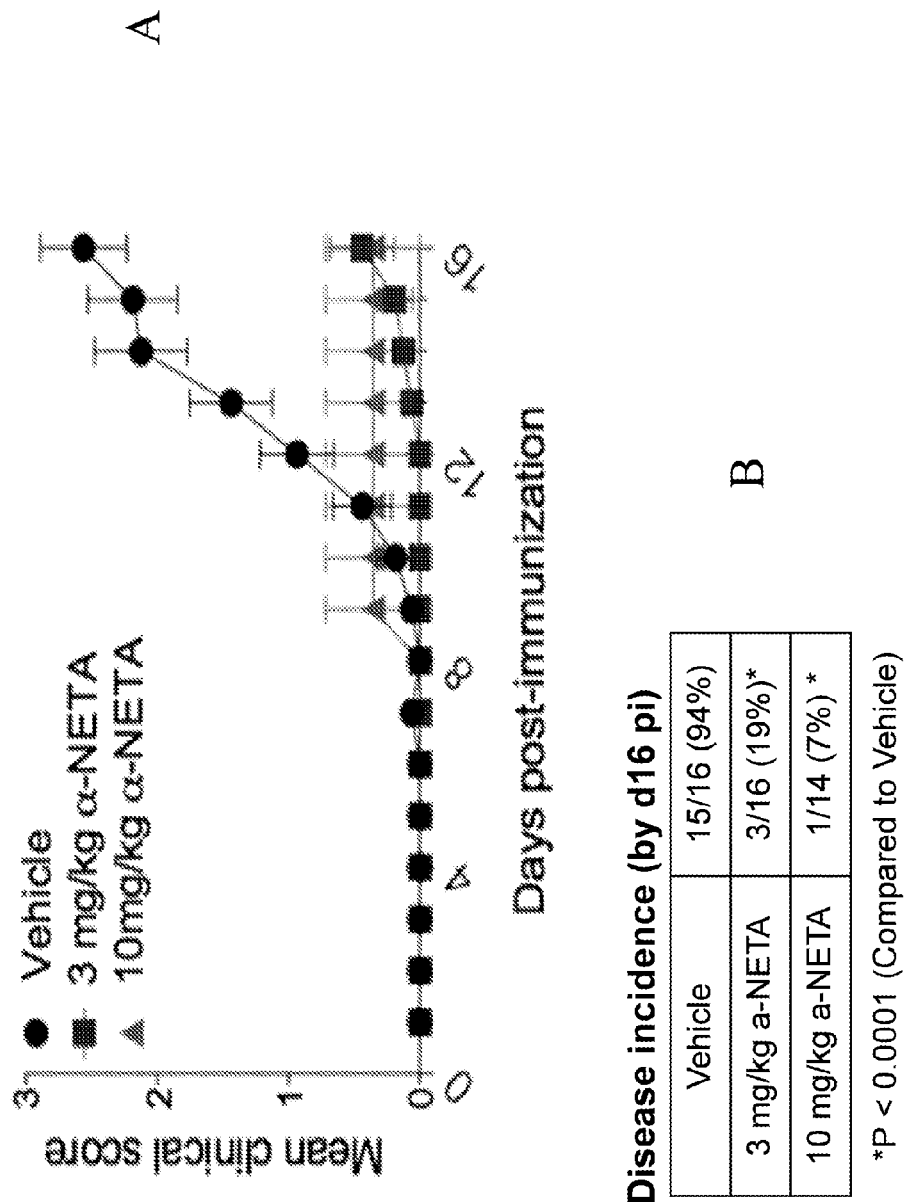
FIG. 13 shows a graph illustrating the result of administration of three different doses of aNETA and controls and the onset of EAE in days post-administration, as well as the disease incidence.

With reference to FIG. 13, With daily administration of 3 mg/kg of aNETA, 19% (3/16) of the animals developed EAE. With daily administration of 10 mg/kg of aNETA, 7% (1/16) developed EAE. In comparison, with administration of the vehicle, 94% (15/16) developed EAE.

Example 15 aNETA Suppresses Leukocyte Infiltration of CNS in EAE

Figure 14:
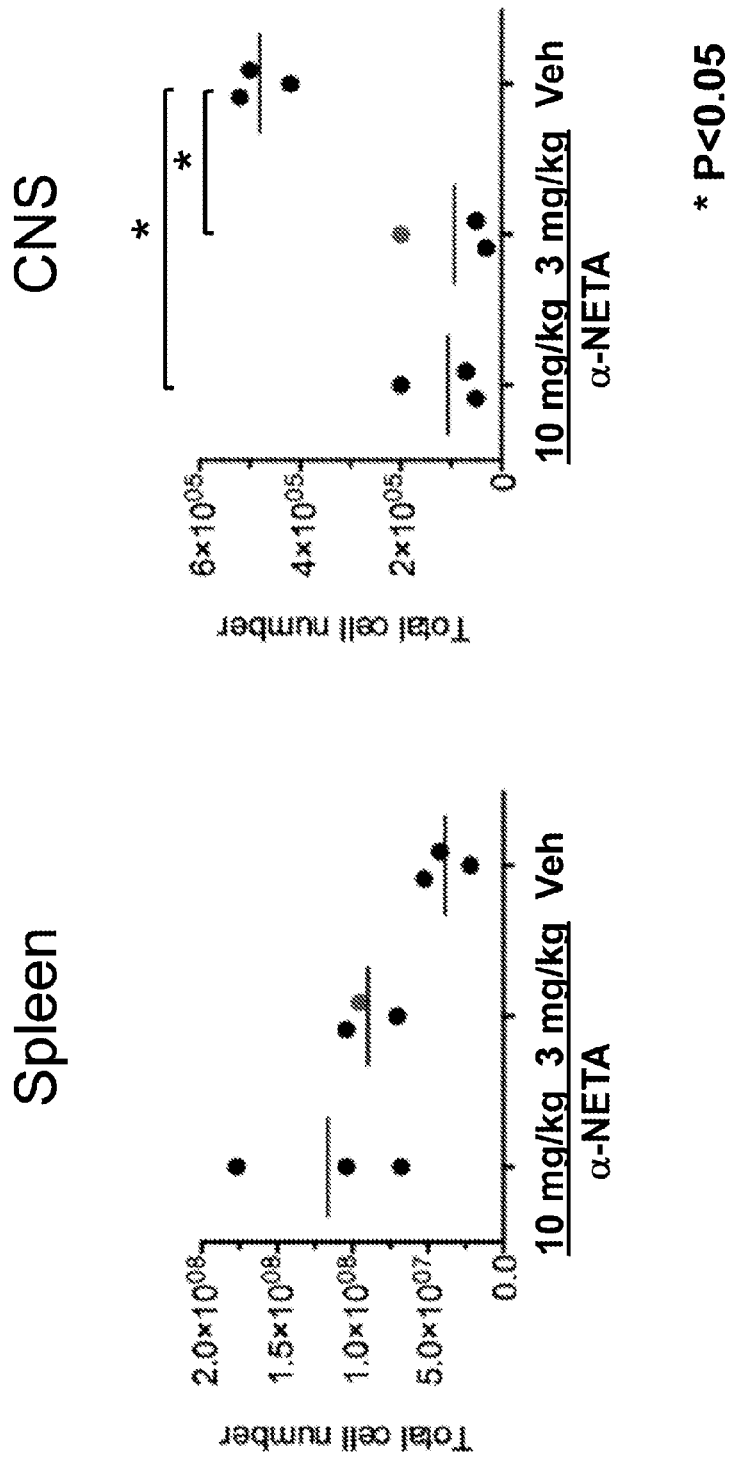
FIG. 14 shows graphs illustrating that aNETA suppresses leukocyte infiltration of CNS in EAE.

With reference to FIG. 14, aNETA suppresses leukocyte infiltration of CNS in EAE. Daily administration aNETA at 10 mg/kg and 3 mg/mg were compared to administration of vehicle. In the spleen, administration aNETA at 10 mg/kg and 3 mg/mg resulted in more leukocytes present. However, with regard to leukocyte infiltration of the CNS, administration aNETA at 10 mg/kg and 3 mg/mg resulted in fewer leukocytes present.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of decreasing demyelinating inflammatory disease in a subject, the method comprising:
administering to said subject an effective amount of a compound of formula (I):

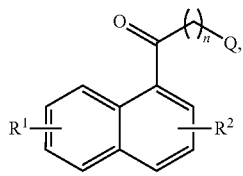

(I)

wherein
Q is selected from $-NR^Q_4{}^+$, $-NH_4{}^+$, $-NH_2$, $-NHR^Q$, $-NR^Q_2$, $-OH$, $-SH$, and lower alkyl; wherein $R^Q$ is lower alkyl; and wherein; Q is selected from $-NR^Q_4{}^+$ or $-NH_4{}^+$, then $X^-$ is present and is a counterion;
$R^1$ and $R^2$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, and sulfonyl; and
n is a number from one to four.

2. The method of claim 1, wherein Q is $-NR^Q_4{}^+$, wherein $R^Q$ is lower alkyl; and wherein $X^-$ is present and is a counterion.

3. The method of claim 2, wherein $X^-$ is selected from fluoride, bromide, chloride, and fluoride.

4. The method of claim 1, wherein $R^1$ and $R^2$ are hydrogen.

5. The method of claim 1, wherein n is two.

6. A method of decreasing demyelinating inflammatory disease in a subject, the method comprising:
administering to said subject an effective amount of a compound of formula (II):

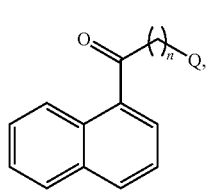

(II)

wherein
Q is selected from $-NR^Q_4{}^+$, $-NH_4{}^+$, $-NH_2$, $-NHR^Q$, $-NR^Q_2$, $-OH$, $-SH$, and lower alkyl; wherein $R^Q$ is lower alkyl; and wherein; Q is selected from $-NR^Q_4{}^+$ or $-NH_4{}^+$, then $X^-$ is present and is a counterion; and
n is a number from one to four.

7. A method of decreasing demyelinating inflammatory disease in a subject, the method comprising:
administering to said subject an effective amount of a compound of formula (III):

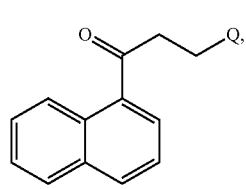

(III)

wherein
Q is selected from $-NR^Q_4{}^+$, $-NH_4{}^+$, $-NH_2$, $-NHR^Q$, $-NR^Q_2$, $-OH$, $-SH$, and lower alkyl; wherein $R^Q$ is lower alkyl; and wherein; Q is selected from $-NR^Q_4{}^+$ or $-NH_4{}^+$, then $X^-$ is present and is a counterion.

8. The method of claim 1, wherein the compound is

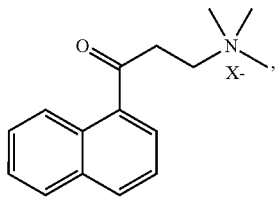

wherein
$X^-$ is selected from iodide, bromide, chloride, and fluoride.

9. The method of claim 1, wherein the compound is

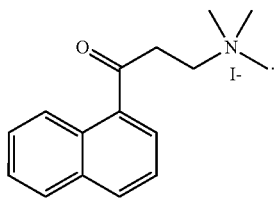

* * * * *